(12) United States Patent
Baron et al.

(10) Patent No.: US 11,664,126 B2
(45) Date of Patent: May 30, 2023

(54) CLINICAL PREDICTOR BASED ON MULTIPLE MACHINE LEARNING MODELS

(71) Applicant: Roche Molecular Systems, Inc., Pleasanton, CA (US)

(72) Inventors: Jason Baron, Somerville, MA (US); M Denise Lamarche Heaney, Alpharetta, GA (US); Matthew Prime, Riehen (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 380 days.

(21) Appl. No.: 16/871,933

(22) Filed: May 11, 2020

(65) Prior Publication Data
US 2021/0350930 A1    Nov. 11, 2021

(51) Int. Cl.
*G06Q 10/10* (2023.01)
*G06Q 10/06* (2023.01)
(Continued)

(52) U.S. Cl.
CPC ............ *G16H 50/20* (2018.01); *G06N 5/003* (2013.01); *G06N 20/20* (2019.01); *G06Q 50/00* (2013.01);
(Continued)

(58) Field of Classification Search
CPC ........ G16H 50/20; G16H 50/30; G16H 50/70; G06N 5/003; G06N 20/20; G06N 5/025;
(Continued)

(56) References Cited

U.S. PATENT DOCUMENTS

| 2008/0033894 A1* | 2/2008 | Steck | G16Z 99/00 706/12 |
| 2010/0057651 A1* | 3/2010 | Fung | G06N 7/005 706/54 |

(Continued)

OTHER PUBLICATIONS

Kong, Y., Yu, T. A Deep Neural Network Model using Random Forest to Extract Feature Representation for Gene Expression Data Classification. Sci Rep 8, 16477 (2018). https://doi.org/10.1038/s41598-018-34833-6 (Year: 2018).*

(Continued)

*Primary Examiner* — Jonathan P Ouellette
(74) *Attorney, Agent, or Firm* — Kilpatrick Townsend and Stockton LLP

(57) ABSTRACT

A method comprises: receiving data corresponding to a plurality of data categories of a patient; selecting, from a plurality of trained machine learning models and based on the plurality of data categories, a first machine learning model and a second machine learning model, the first machine learning model being trained using first data of a first subset of the plurality of data categories and having a first weight indicative of a first performance metric value, the second machine learning model being trained using second data of a second subset of the plurality of data categories and having a second weight indicative of a second performance metric value; generating a first prediction result and a second prediction result using, respectively, the first model and the second model; and generating a combined prediction result based on the first prediction result, the second prediction result, the first weight and the second weight.

20 Claims, 17 Drawing Sheets

(51) Int. Cl.
- *G06Q 30/02* (2023.01)
- *G06Q 30/06* (2023.01)
- *G16H 50/20* (2018.01)
- *G16H 50/30* (2018.01)
- *G06N 20/20* (2019.01)
- *G06N 5/00* (2023.01)
- *G06Q 50/00* (2012.01)
- *G06K 9/62* (2022.01)

(52) U.S. Cl.
CPC .......... *G16H 50/30* (2018.01); *G06K 9/6227* (2013.01); *G06K 9/6262* (2013.01); *G06K 9/6289* (2013.01)

(58) Field of Classification Search
CPC .... G06Q 50/00; G06K 9/6227; G06K 9/6262; G06K 9/6289
USPC .................................................. 705/1.1–912
See application file for complete search history.

(56) References Cited

U.S. PATENT DOCUMENTS

| | | | |
|---|---|---|---|
| 2011/0082712 A1* | 4/2011 | Eberhardt, III | G16H 50/30 705/4 |
| 2018/0168516 A1* | 6/2018 | Pappada | G16H 50/50 |
| 2018/0374583 A1* | 12/2018 | Goldstein | G06G 1/14 |
| 2019/0316209 A1* | 10/2019 | Hubbell | C12Q 1/6806 |
| 2020/0105413 A1* | 4/2020 | Vladimirova | G06T 7/0012 |
| 2020/0181710 A1* | 6/2020 | Steelman | A61B 10/02 |

OTHER PUBLICATIONS

International Search Report and Written Opinion in PCT/US2021/031612 dated Aug. 18, 2021; 17 pages.
Utkin, L.V. et al.; "A weighted random survival forest"; ARXIV.org: Cornell University Library; Ithaca, NY; Jan. 1, 2019; 21 pages.
Gajowniczek K. et al.; "Weighted Random Forests to Improve Arrhythmia Classification"; *Electronics*; vol. 9, No. 1; Jan. 3, 2020; 20 pages.

* cited by examiner

220 →

| Category | Type |
|---|---|
| Gender | Biography |
| Age | Biography |
| Race | Biography |
| GroupStage | History |
| Colorectal Site | History |
| SmokingStatus | History |
| leukocytes | Lab |
| hemoglobin | Lab |
| platelets | Lab |
| hematocrit | Lab |
| erythrocytes | Lab |
| creatinine | Lab |
| lymphocytes | Lab |
| protein | Lab |
| bilirubin | Lab |
| urea.nitrogen | Lab |
| carcinoembryonic.ag | Lab |
| calcium | Lab |
| sodium | Lab |
| potassium | Lab |
| alkaline.phosphatase | Lab |
| carbon.dioxide | Lab |
| monocytes | Lab |
| chloride | Lab |
| lactate.dehydrogenase | Lab |
| glucose | Lab |
| BRAF | Biomarker |
| ER | Biomarker |
| PR | Biomarker |
| HER2 | Biomarker |
| EGFR | Biomarker |
| ALK | Biomarker |
| KRAS | Biomarker |

FIG. 2B

| Variables | Type | Advanced Lung Cancer $LC_A - LC_H$ | | | | | | | | | Metasastic Breast Cancer $BC_A - BC_E$ | | | | | Metasastic Colorectal Cancer $CRC_A - CRC_G$ | | | | | | |
|---|---|---|---|---|---|---|---|---|---|---|---|---|---|---|---|---|---|---|---|---|---|---|
| | | A | B | C | D | E | F | G | H | rm | A | B | C | D | E | A | B | C | D | E | F | G |
| Gender | Biography | 1 | 0 | 1 | 1 | 0 | 1 | 1 | 1 | 0 | 1 | 0 | 1 | 1 | 1 | 1 | 0 | 1 | 1 | 1 | 1 | 1 |
| Age | Biography | 0 | 1 | 1 | 1 | 0 | 1 | 1 | 1 | 0 | 0 | 1 | 1 | 1 | 1 | 0 | 1 | 1 | 1 | 1 | 1 | 1 |
| Race | Biography | 1 | 0 | 1 | 1 | 0 | 1 | 1 | 1 | 0 | 1 | 0 | 1 | 1 | 1 | 1 | 0 | 1 | 1 | 1 | 1 | 1 |
| CrcSite | History | 0 | 0 | 0 | 0 | 0 | 0 | 0 | 0 | 0 | 0 | 0 | 0 | 0 | 0 | 0 | 1 | 1 | 1 | 1 | 1 | 1 |
| Histology | History | 0 | 1 | 1 | 1 | 0 | 1 | 1 | 1 | 0 | 0 | 0 | 0 | 0 | 0 | 0 | 0 | 0 | 0 | 0 | 0 | 0 |
| Smoking Status | History | 0 | 1 | 1 | 1 | 0 | 1 | 1 | 1 | 0 | 0 | 0 | 0 | 0 | 0 | 0 | 0 | 0 | 0 | 0 | 0 | 0 |
| leukocytes | Lab | 0 | 0 | 0 | 1 | 0 | 0 | 1 | 1 | 0 | 0 | 0 | 0 | 0 | 1 | 0 | 0 | 0 | 1 | 1 | 1 | 1 |
| hemoglobin | Lab | 0 | 0 | 0 | 1 | 0 | 0 | 1 | 1 | 0 | 0 | 0 | 0 | 0 | 1 | 0 | 0 | 0 | 1 | 1 | 1 | 1 |
| platelets | Lab | 0 | 0 | 0 | 1 | 0 | 0 | 1 | 1 | 0 | 0 | 0 | 0 | 0 | 1 | 0 | 0 | 0 | 1 | 1 | 1 | 1 |
| hematocrit | Lab | 0 | 0 | 0 | 1 | 0 | 0 | 1 | 1 | 0 | 0 | 0 | 0 | 0 | 1 | 0 | 0 | 0 | 1 | 1 | 1 | 1 |
| erythrocytes | Lab | 0 | 0 | 0 | 1 | 0 | 0 | 1 | 1 | 0 | 0 | 0 | 0 | 0 | 1 | 0 | 0 | 0 | 1 | 1 | 1 | 1 |
| ceratinine | Lab | 0 | 0 | 0 | 1 | 0 | 0 | 1 | 1 | 0 | 0 | 0 | 0 | 0 | 1 | 0 | 0 | 0 | 1 | 1 | 1 | 1 |
| lymphocytes | Lab | 0 | 0 | 0 | 1 | 0 | 0 | 1 | 1 | 0 | 0 | 0 | 0 | 0 | 1 | 0 | 0 | 0 | 1 | 1 | 1 | 1 |
| proteins | Lab | 0 | 0 | 0 | 1 | 0 | 0 | 1 | 1 | 0 | 0 | 0 | 0 | 0 | 1 | 0 | 0 | 0 | 1 | 1 | 0 | 0 |
| bilirubin | Lab | 0 | 0 | 0 | 0 | 0 | 0 | 0 | 0 | 0 | 0 | 0 | 0 | 0 | 1 | 0 | 0 | 0 | 1 | 1 | 1 | 1 |
| urea.nitrogen | Lab | 0 | 0 | 0 | 0 | 0 | 0 | 0 | 0 | 0 | 0 | 0 | 0 | 0 | 0 | 0 | 0 | 0 | 1 | 1 | 1 | 1 |
| carcinoembryonic.ag | Lab | 0 | 0 | 0 | 0 | 0 | 0 | 0 | 1 | 0 | 0 | 0 | 0 | 0 | 0 | 0 | 0 | 0 | 0 | 1 | 1 | 1 |
| calcium | Lab | 0 | 0 | 0 | 0 | 0 | 0 | 0 | 0 | 0 | 0 | 0 | 0 | 0 | 1 | 0 | 0 | 0 | 1 | 1 | 0 | 0 |
| sodium | Lab | 0 | 0 | 0 | 0 | 0 | 0 | 0 | 0 | 0 | 0 | 0 | 0 | 0 | 1 | 0 | 0 | 0 | 1 | 1 | 0 | 0 |
| potassium | Lab | 0 | 0 | 0 | 0 | 0 | 0 | 0 | 0 | 0 | 0 | 0 | 0 | 0 | 1 | 0 | 0 | 0 | 1 | 1 | 0 | 0 |
| alkaline.phosphatase | Lab | 0 | 0 | 0 | 0 | 0 | 0 | 0 | 0 | 0 | 0 | 0 | 0 | 0 | 1 | 0 | 0 | 0 | 1 | 1 | 0 | 0 |
| lymphocytes.per.100.leukocytes | Lab | 0 | 0 | 0 | 0 | 0 | 0 | 0 | 0 | 0 | 0 | 0 | 0 | 0 | 1 | 0 | 0 | 0 | 1 | 1 | 0 | 0 |
| monocytes.per.100.leukocytes | Lab | 0 | 0 | 0 | 0 | 0 | 0 | 0 | 1 | 0 | 0 | 0 | 0 | 0 | 0 | 0 | 0 | 0 | 0 | 0 | 0 | 0 |
| Carbon Dioxide | Lab | 0 | 0 | 0 | 0 | 0 | 0 | 0 | 1 | 0 | 0 | 0 | 0 | 0 | 0 | 0 | 0 | 0 | 0 | 0 | 0 | 0 |
| monocytes | Lab | 0 | 0 | 0 | 0 | 0 | 0 | 0 | 1 | 0 | 0 | 0 | 0 | 0 | 0 | 0 | 0 | 0 | 0 | 0 | 0 | 0 |
| chloride | Lab | 0 | 0 | 0 | 0 | 0 | 0 | 0 | 1 | 0 | 0 | 0 | 0 | 0 | 0 | 0 | 0 | 0 | 0 | 0 | 0 | 0 |
| lactate.dehydrogenase | Lab | 0 | 0 | 0 | 0 | 0 | 0 | 0 | 1 | 0 | 0 | 0 | 0 | 0 | 0 | 0 | 0 | 0 | 0 | 0 | 0 | 0 |
| glucose | Lab | 0 | 0 | 0 | 0 | 0 | 0 | 0 | 0 | 0 | 0 | 0 | 0 | 1 | 1 | 0 | 0 | 0 | 1 | 1 | 0 | 0 |
| ER | Biomarker | 0 | 0 | 0 | 0 | 0 | 0 | 0 | 0 | 0 | 0 | 0 | 0 | 1 | 1 | 0 | 0 | 0 | 0 | 0 | 0 | 0 |
| PR | Biomarker | 0 | 0 | 0 | 0 | 0 | 0 | 0 | 0 | 0 | 0 | 0 | 0 | 1 | 1 | 0 | 0 | 0 | 0 | 0 | 0 | 0 |
| HER2 | Biomarker | 0 | 0 | 0 | 0 | 0 | 0 | 0 | 0 | 0 | 0 | 0 | 0 | 1 | 1 | 0 | 0 | 0 | 0 | 0 | 0 | 0 |
| EGFR | Biomarker | 0 | 0 | 0 | 0 | 1 | 1 | 1 | 1 | 0 | 0 | 0 | 0 | 0 | 0 | 0 | 0 | 0 | 0 | 0 | 0 | 0 |
| ALK | Biomarker | 0 | 0 | 0 | 0 | 1 | 1 | 1 | 1 | 0 | 0 | 0 | 0 | 0 | 0 | 0 | 0 | 0 | 0 | 0 | 0 | 0 |
| KRAS | Biomarker | 0 | 0 | 0 | 0 | 0 | 0 | 0 | 0 | 0 | 0 | 0 | 0 | 0 | 0 | 0 | 0 | 0 | 0 | 0 | 1 | 1 |
| BRAF | Biomarker | 0 | 0 | 0 | 0 | 0 | 0 | 0 | 0 | 0 | 0 | 0 | 0 | 0 | 0 | 0 | 0 | 0 | 0 | 0 | 0 | 1 |
| Random number | Numerical | 0 | 0 | 0 | 0 | 0 | 0 | 0 | 0 | 0 | 1 | 0 | 0 | 0 | 0 | 0 | 0 | 0 | 0 | 0 | 0 | 0 |

FIG. 4A

| Cancer Type | Prediction models | # of Complete Cases | # of Entire Cohort |
|---|---|---|---|
| Metastatic CRC | $CRC_A$ | 8758 | 100% |
| | $CRC_B$ | 8761 | 100% |
| | $CRC_C$ | 8758 | 100% |
| | $CRC_D$ | 4314 | 49% |
| | $CRC_E$ | 3759 | 43% |
| | $CRC_F$ | 3030 | 35% |
| | $CRC_G$ | 1305 | 15% |
| | Entire Cohort | 8761 | 100% |
| Metastatic Breast Cancer | $BC_A$ | 7226 | 100% |
| | $BC_B$ | 7226 | 100% |
| | $BC_C$ | 7226 | 100% |
| | $BC_D$ | 6828 | 94% |
| | $BC_E$ | 3811 | 53% |
| | Entire Cohort | 7226 | 100% |
| Advanced Lung Cancer | $LC_A$ | 11733 | 100% |
| | $LC_B$ | 11734 | 100% |
| | $LC_C$ | 11733 | 100% |
| | $LC_D$ | 7420 | 63% |
| | $LC_E$ | 5749 | 49% |
| | $LC_F$ | 5748 | 49% |
| | $LC_G$ | 3757 | 32% |
| | $LC_H$ | 239 | 2% |
| | Entire Cohort | 11734 | 100% |

FIG. 4B

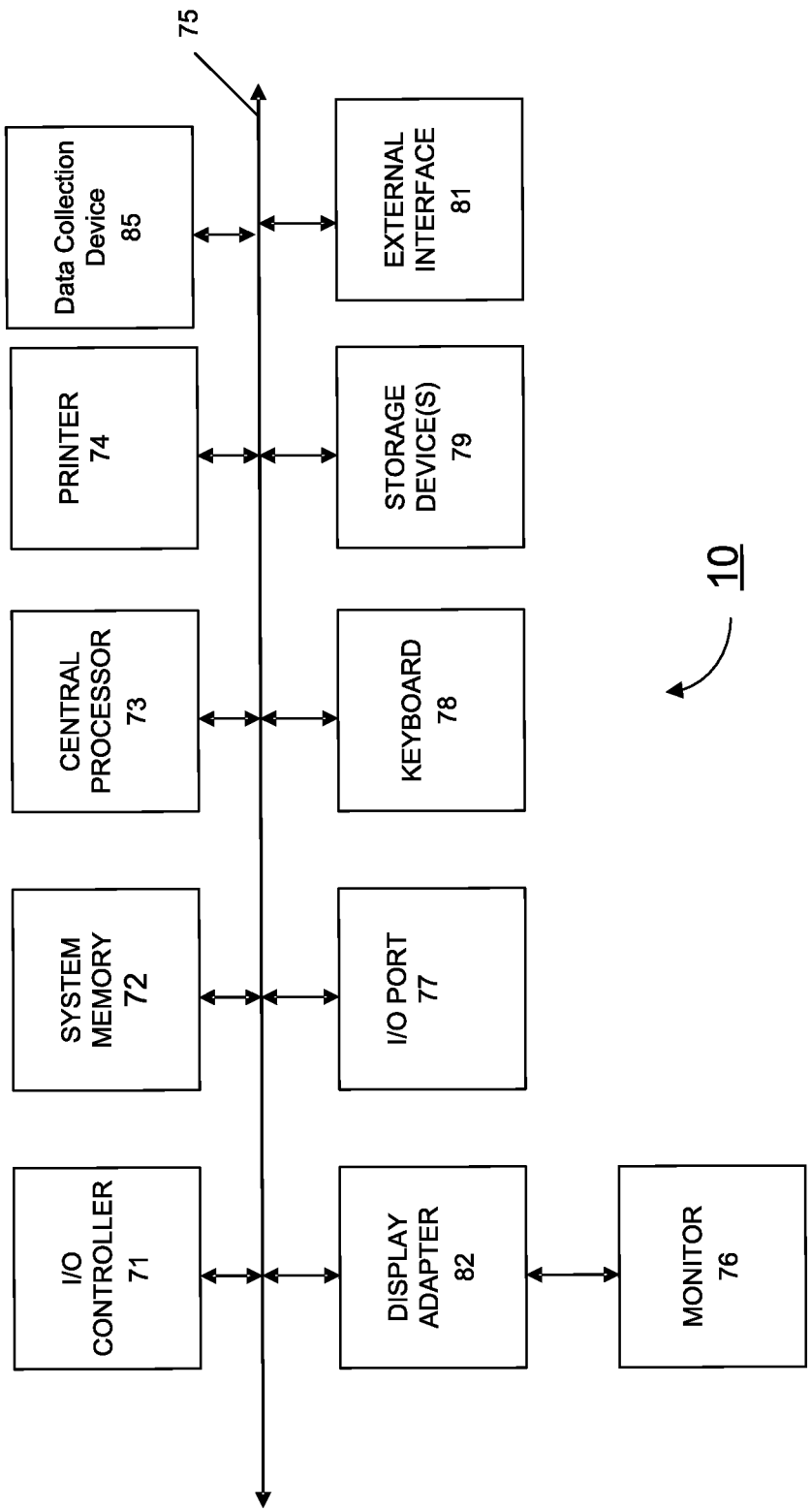

CLINICAL PREDICTOR BASED ON MULTIPLE MACHINE LEARNING MODELS

BACKGROUND

Predictive machine learning models trained using real world clinical data offer tremendous potential to provide patients and their clinicians patient-specific information regarding diagnosis, prognosis, or optimal therapeutic course. Machine learning models can be trained, for example, to predict the likelihood of a patient surviving as a function of time from a diagnosis (e.g., an advanced stage cancer). Survival predictions can also be stratified based on the treatment the patient will receive. A clinical decision, such as the treatment to be administered to the patient, can then be made by the physician in part based on the prediction (e.g. the physician would often favor the treatment with the longest predicted survival). The prognosis information can also be provided to the patient to, for example, improve the patient's ability to plan for his/her future, which can improve the quality of life of the patient.

A machine learning model can be trained to perform a prediction for a patient based on patient data comprising a plurality of data categories. The application of the machine learning model in performing the prediction can be limited when certain data categories are missing in the patient data. A machine learning model requiring predictor data from one set of data categories may be unable to perform predictions using real patient data that include only a subset of the required categories. For example, a model that makes predictions based on hematology and molecular laboratory test results may not be able to make predictions for a patient that has the hematology data but not molecular test results.

BRIEF SUMMARY

Disclosed herein are techniques for performing a clinical prediction based on a meta-model comprising a plurality of machine learning models. The clinical prediction can include, for example, predicting a survival rate of a patient at a time point from a diagnosis of a disease. Each machine learning model can be trained using a different set of data categories including, for example, biographical data, medical history data, laboratory test results, biomarkers, etc. Each machine learning model can also be associated with a weight indicative of a performance metric such as, for example, an area under curve (AUC) of a receiver operating characteristic (ROC) curve of the machine learning model.

To perform the clinical prediction for a particular patient, a plurality of machine learning models can be identified based on the data categories present in the patient's data. Each of the identified machine learning models can be trained with clinical data of other patients associated with a particular subset of the data categories present in the patient's data. Subsets of the patient's data associated with the subset of data categories can be extracted and input to the associated machine learning models to generate prediction results. The prediction results from the machine learning models can be combined based on the weights of the machine learning models to generate a combined prediction result for the patient.

These and other embodiments of the invention are described in detail below. For example, other embodiments are directed to systems, devices, and computer readable media associated with methods described herein.

A better understanding of the nature and advantages of embodiments of the present invention may be gained with reference to the following detailed description and the accompanying drawings.

BRIEF DESCRIPTION OF THE DRAWINGS

The detailed description is set forth with reference to the accompanying figures.

FIG. 2A, FIG. 2B, FIG. 2C, and FIG. 2D illustrate examples of performing clinical predictions using a machine learning model, according to certain aspects of this disclosure.

FIG. 4A, FIG. 4B, FIG. 4C, FIG. 4D, and FIG. 4E illustrate examples of experiment results of performing clinical predictions using a meta-model, according to certain aspects of this disclosure.

FIG. 6 illustrates an example computer system that may be utilized to implement techniques disclosed herein.

DETAILED DESCRIPTION

Figure 1A:
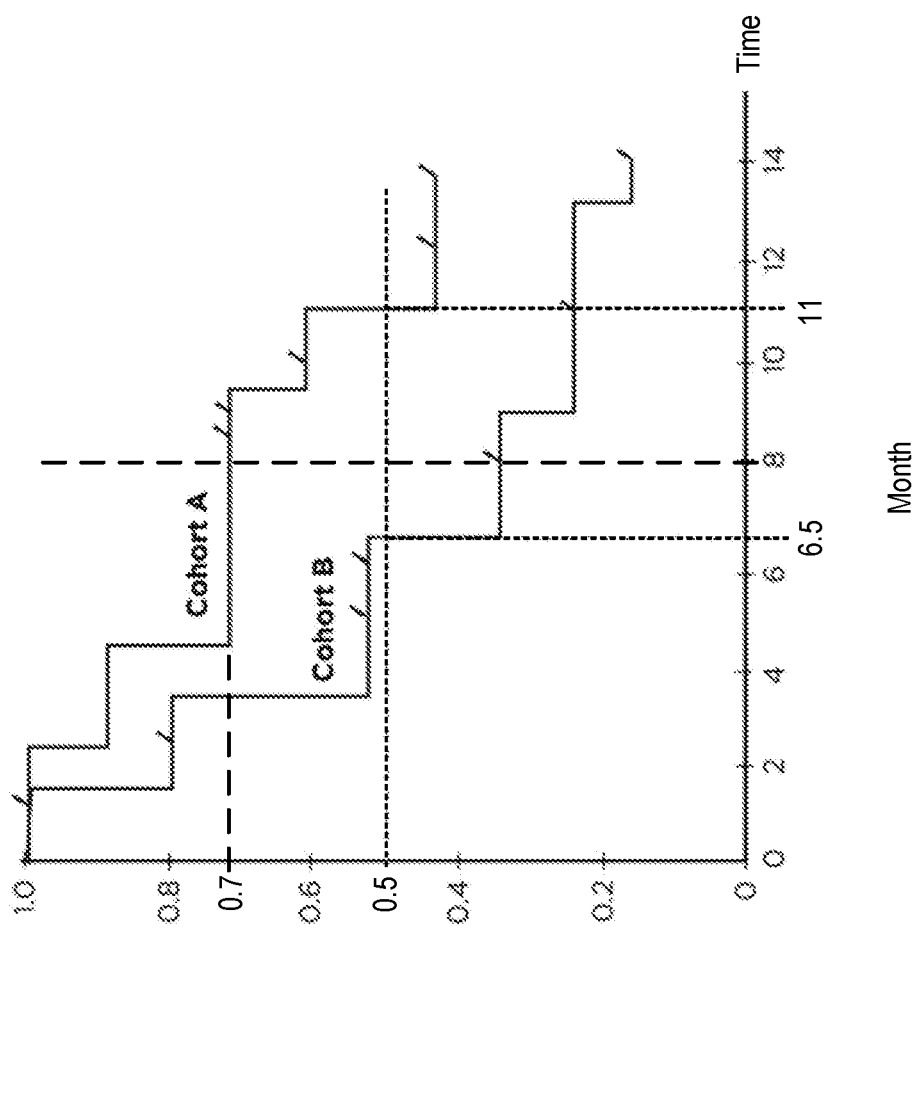
FIG. 1A and FIG. 1B illustrate examples of clinical predictions that can be performed using techniques described in this disclosure.

According to embodiments of the disclosure, a machine learning model can be trained to perform a clinical prediction for a patient based on patient data comprising a set data categories. The clinical prediction may include, for example, predicting a survival rate of a patient as a function of time from a diagnosis (e.g., an advanced stage cancer). The prediction of survival rate can also be made for different types of treatments. A machine learning predictive model of the present disclosure can be a very powerful tool for performing a clinical prediction and assisting a clinician in generating a clinical decision based on the prediction result, since the model can expose hidden relationships between a clinical parameter to be predicted (e.g., survival rate) and various data categories of patient data that are otherwise not considered by the clinician. The machine learning model can be trained using the data of a very large population of patients to learn various relationship between the clinical parameter and the various data categories, and then perform a prediction for a patient based on the patient data and the relationships the model has learnt through training.

Although a machine learning predictive model can be very powerful in performing a clinical prediction and in assisting a clinician in generating a clinical decision, key challenges have limited the introduction of machine learning-based predictive models into real clinical settings. One set of challenges relates to inter-patient variability in data availability. In most real world datasets, many patients will lack recorded findings for many data categories. On the other hand, a machine learning model is typically trained using data of a large set of data categories to expose more hidden links between the parameter to be predicted and the large set of data categories. If a machine learning model is trained to make a prediction based on a set of data categories, but the patient data lack one or more categories from the set, the machine learning model may be unable to perform a prediction based on the patient data.

The data categories included in the data of a group of patients can vary among different patients due to various reasons, which leads to large data heterogeneity. For example, some hospitals may have a laboratory test menu that includes more than 1,000 unique orderable tests. Depending on the patients' situation (e.g., clinical setting, clinical conditions and diagnoses, clinical severity, comorbidities, treatments received, age, gender, economic condition, etc.), most patients may have had at most a small fraction of these possible tests, and the patients may have different fractions of these tests. As another example, different patients may lack different categories of non-laboratory clinical data, including other diagnostic studies, elements of patient history, biopsy data, etc. The issue of data heterogeneity becomes particularly significant when considering time series data; even patients who have similar diagnostic tests or physical exam maneuvers may have them performed at different time points or repeated at varying intervals. In all these cases, due to the various missing data categories in the patients' data, the machine learning model may be unable to perform a prediction for a large number of patients, which limits the utility of the machine learning model.

One approach to overcome the challenges posted by data heterogeneity to machine learning model is by an imputation process, in which a set of clinical data of a patient can be pre-processed to create additional clinical data elements for the missing data categories, so that the patient data, including the original and imputed clinical data elements, can include the full set of data categories as input to the machine learning model. The imputation process can estimate a distribution or value of each data element of the missing data categories based on the original patient data. The imputation process, however, can have major limitations. Specifically, most imputation algorithms assume data are "missing at random" (MAR), but the MAR assumption is typically not valid for most clinical data. This is because the diagnostic studies that generate the clinical data are selected and ordered in response to the clinical setting, not by random, therefore the presence (or absence) of a certain data category in a patient data is also not random. Moreover, imputation can introduce additional uncertainty and inaccuracy into predictions and may obscure some of the hidden relationship between the predicted parameter and the data categories.

Disclosed herein are techniques for performing a clinical prediction using a combined learning model (herein after, a "meta-model") comprising a plurality of machine learning models, to address some of the issues above. Each of the plurality of machine learning models in the meta-model is separately trained using data of a set of data categories, and different machine learning models are trained using data of different sets of data categories, although there can be overlapping data categories among the different sets. In a case where the machine learning models are trained to predict the survival rates of the patients, the training of the machine learning models can be based on, for example, classifying patients into groups such that the similarity in the survival statistics of patients within a group is maximized, while the difference in the survival statistics of patients between the groups is maximized. Each of the plurality of machine learning models can be associated with a performance metric, which can be obtained from a validation process of the trained machine learning model. In a case where the machine learning model is trained to predict a survival rate of a patient, the performance metrics can measure a relationship between the true positive rates and false positive rates output by the model, which can be represented in the form of a receiver operating characteristic (ROC) curve. In some examples, the performance metrics can be based on the area under curve (AUC) of the ROC curve of the model.

Each of the plurality of machine learning models can be used to perform a clinical prediction for a patient. The patient data may include a plurality of data categories, which can be mapped to the different sets of data categories of the plurality of machine learning models. Based on the mapping, a meta-model comprising at least a first machine learning model and a second machine learning model, each trained using data of different subsets of the data categories in the patient data, can be selected. For example, the first machine learning model is trained using data of a first subset of the plurality of data categories, whereas the second machine learning model is trained using data of a second subset of the plurality of data categories. A first subset of the patient data corresponding to the first subset of the plurality of data categories can be input to the first machine learning model to generate a first prediction output, whereas a second subset of the plurality of data categories can be input to the second machine learning model to generate a second prediction output. The meta-model can then generate a combined prediction output based on the first prediction output, the first performance metric, the second prediction output, and the second performance metric. A clinical prediction can then be made based on the combined prediction output.

In some examples, the plurality of data categories can include various biographical information, such as age and gender of the patient, each of which can correspond to a data category. The plurality of data categories may also include a history of the patient, such as a treatment history of the patient (e.g., which treatment(s) the patient has received), a habit of the patient (e.g., whether the patient smokes), etc. The plurality of data categories may also include different categories of laboratory test results of the patient, such as a leukocytes count, a hemoglobin count, a platelets count, a hematocrit count, an erythrocyte count, a creatinine count, a lymphocytes count, measurements of protein, bilirubin, calcium, sodium, potassium, glucose, etc., with each category of laboratory test result corresponding to a data category. The plurality of data categories may also indicate measurements of various biomarkers for different cancer types, such as estrogen receptor (ER), progesterone receptor (PR), human epidermal growth factor receptor 2 (HER2), epidermal growth factor receptor (EGFR, or HER1) for breast cancer, ALK (anaplastic lymphoma kinase) for lung cancer, KRAS gene for lung and colorectal cancers, BRAF gene for colorectal cancer, etc. Each biomarker measurement can also correspond to a data category. Each machine learning model of the plurality of machine learning models can be trained using different subsets of the plurality of data categories (e.g., different subsets of the biographical information, different subsets of the laboratory test results, different subsets of the biomarker measurements, etc.) to perform a prediction.

In some examples, the plurality of machine learning models can be trained to determine a survival rate of a patient as a function of time. The survive rate can predict a likelihood that the patient survives at a pre-determined time (e.g., 500 days, 1000 days, 1500 days, etc.) after the patient is diagnosed of a medical condition (e.g., an advanced stage cancer). The survival rates with respect to time can be used to generate a patient-specific Kaplan-Meier (KM) plot for the patient. The machine learning models can be implemented using different techniques, such as a random forest model, a regression model, etc.

Specifically, the random forest model may include a plurality of decision trees, with each tree associated with a different set of data categories. Each decision tree can include multiple terminal nodes, with each terminal node associated with a value of a cumulative hazard function (CHF) and representing a particular combination of ranges of data values of the set of data categories. A cumulative hazard function can be interpreted as the probability of survival (or death) of a patient at a particular time from a diagnosis, given that the patient survives at least until that particular time. Each decision tree in a random forest model can classify the patient into one of the terminal nodes based on the values of the corresponding data categories of the patient and output a value of the cumulative hazard function of the patient. The values from the decision trees of a random forest model can be averaged as the cumulative hazard function output of the patient, and a predicted survival rate of the patient can be computed based on the cumulative hazard function output.

On the other hand, a regression model, such as a proportional hazards regression model, can include a set of parameters which can be combined with the data values of a patient to compute the cumulative hazard function of the patient. Multiple random forest models and/or regression models, each associated with a particular time from when the diagnosis is made, can be provided to output different values of the cumulative hazard function, which can be used to generate predicted survival rates of a patient as a function of time.

A training process can generate: (1) each decision tree in a random forest model, (2) the data categories assigned to each decision tree, (3) the classification criteria at each parent node of the decision trees, and (4) the value of the cumulative hazard function at each terminal node. The training process can use patient data of a set of data categories, as well as survival statistics, of a large population of patients. Specifically, the training process can start with randomly assigning a subset of the data categories to a root node of a decision tree, and different subsets of the data categories can be assigned to the root nodes of different decision trees. Moreover, in a bagging process, each decision tree can obtain a random set of samples of the patient data of the assigned subset of the data categories. The root node (and each parent node thereafter) can then be split into child nodes in a recursive node-splitting process.

In the node-splitting process, a node representing a set of patients can be split into two child nodes each representing a subset of the patient based on thresholds for the subset of the data categories, with the subset of the data categories and thresholds selected to maximize a difference in the number of surviving patients/deaths between the two child nodes. The process can then be repeated on the child nodes to generate additional child nodes until, for example, a threshold minimum number of deaths/non-survival patients is reached in a particular child node, which can then become a terminal node. The patients can then be classified into the terminal nodes by the decision tree according to their values of the subset of data categories. The cumulative hazard function output at each terminal node can be represented by a percentage of the surviving patients classified into the terminal node.

In addition, a proportional hazards regression model can also be trained to perform the prediction. The regression model can include coefficients that relate different data categories of a patient to a probability of survival (e.g., a cumulative hazard function) at a pre-determined time after diagnosis. Based on the regression model, as well as the values of the patient for the different data categories as inputs, the probability of the patient surviving at the pre-determined time can also be computed as outputs of the regression model. The parameters of the regression model can also be determined in a training process that includes fitting of the regression model over patients' data of the different data categories, as well as survival statistics of the patients, of a large population of patients. For example, based on the survival statistics, a percentage of the surviving patients in the group (with the group size adjusted with respect to time to account for deaths) at different times can be determined to represent the target survival rate. The regression model parameters can then be determined based on the values of the patients for the different data categories at different times, such that the regression model outputs the target survival rates.

As described above, each of the plurality of machine learning models can be associated with a performance metric, which can be used to generate the combined output of the meta-model. The performance metric can indicate a degree of confidence that a particular machine learning model generates a correct prediction. The performance metric of a machine learning model can be determined using various techniques, such as determining the area under the receiver operating characteristic (ROC) curve of the machine learning model. The ROC curve can provide a plot between corresponding true positive rates and false positive rates of the machine learning model. A value of 0.5 for the area under ROC, meaning that the true positive rate and the false positive rate are equal on average, can indicate the machine learning model cannot discriminate and is undesirable, while a larger area under the ROC, exceeding 0.5, can indicate a higher of confidence in the prediction. A weight can be assigned to a machine learning model based on the area of the ROC of the machine learning model, with a larger weight assigned to a machine learning model having a larger area of the ROC and vice versa. The combined prediction output can be generated based on a weighted average of the prediction outputs of the machine learning models, with each prediction output scaled by a respective weight of the machine learning model.

In a case where the machine learning models are trained to output a survival rate of a patient, a true positive occurs when the machine learning model outputs that the survival probability of the patient, at a given time, exceeds a probability threshold and the patient actually survives at that given time. A false positive occurs when the survival probability of the patient exceeds the probability threshold, but the patient does not survive at that given time. A validation process can be performed in which the data of a group of patient is input to the machine learning model to compute the survival rate of each patient. To determine the performance metrics, a true positive rate representing a percentage of the patients having the survival rate exceeding the probability threshold and surviving, and a corresponding false positive rate representing the percentage of patients having the survival rate exceeding the probability threshold and not surviving, can be obtained for a range of probability thresholds. Different pairs of true positive rate and false positive rate for different probability thresholds can then be determined to generate the ROC plot, and the area under the ROC can be determined for the machine learning model. In various implementations, true negative rates and/or false negative rates may be used in addition or instead of the true positive rate and/or the false positive rate.

The training of each machine model, as well as the determination of the performance metrics of the machine model, can be performed based on different subsets of patient data of the same group of patients in a cross-validation process. Specifically, from the patient data of a group of patients, patients having data including the data categories required by the machine learning model can be identified. The identified patients can be divided into two subsets. One subset (e.g., the patient data of 80% of the patients) can be used to train the machine model, while the other subset (e.g., the patient data of the remaining 20% of the patients) can be input into the trained machine model to generate the ROC plot and to compute the area under the ROC as part of a cross-validation process. In some examples, the training and the cross-validation can be repeated using different subsets of the patient data (e.g., different 80% and 20% portions of the patients) for each iteration, and the weight assigned to the machine learning model can be determined by averaging the ROC areas from the multiple iterations. The training process can be repeated for a second machine learning model, beginning with identifying patients having data including data categories required by the second machine learning model. With more iterations of training and cross-validation, the confidence level of the machine learning models in generating the correct predictions can be improved.

With the disclosed embodiments, instead of using a single machine learning model trained with a large and fixed set of data categories to perform a clinical prediction for a patient, a meta-model comprising multiple machine learning models, each trained with a smaller but different set of data categories, can be provided to perform the clinical prediction for the patient. The machine learning models of the meta-model can be selected based on the data categories of the patient data matching the data categories of the machine learning models, such that there is no missing data category in the patient data for the selected machine learning models. This can reduce or eliminate the need to impute data elements from the patient data for the machine learning model, as well as the uncertainty in the prediction caused by the imputed data. The reduced number of data categories input to a machine learning model can also reduce the number of possible permutations of inputs to the machine learning model, which can reduce the training time (or at least make the training more manageable) for the machine learning model. Moreover, as the prediction outputs of the selected machine learning models are combined to generate the combined prediction output, the combined prediction output can reflect all data categories present in the patient data, while the combination also reflects the confidence level of each machine learning model. All these can improve the confidence level of the clinical prediction produced by the meta-model. Further, in a case where the clinical prediction is used to predict the survival rate of a patient in response to a treatment, the prediction can also be made more accurately and earlier in the patient journey, and a corrective action, such as consideration of additional therapeutic options, available clinical trials, etc., can also be performed earlier. All these can increase the odds of recovery and survival of the patient.

I. Examples of Clinical Prediction and Application

Figure 1B:
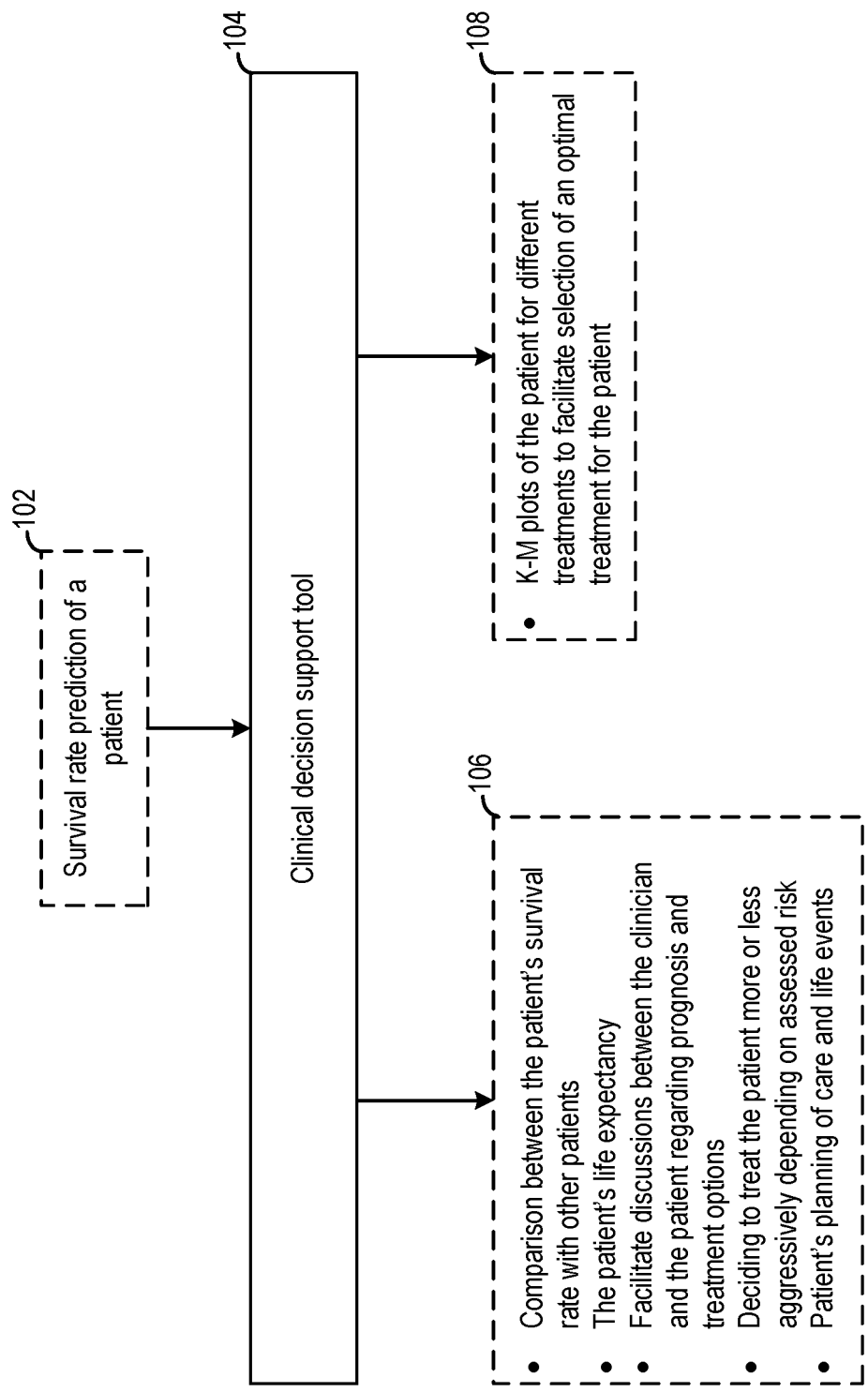

FIG. 1A and FIG. 1B illustrate examples of a clinical prediction that can be provided by examples of the present disclosure. FIG. 1A illustrates a mechanism to predict a survival rate of a patient with respect to time from when a diagnosis of a cancer is made, whereas FIG. 1B illustrates example applications of survival rate prediction. Referring to FIG. 1A, chart 100 illustrates examples of a Kaplan-Meier (K-M) plot, which provides a study of survival statistics among patients having a type of cancer (e.g., lung cancer). The patients may receive a particular treatment. A K-M plot shows the change of survival rate of a group of patients with respect to time measured from when the patients are diagnosed with the cancer. In a case where the patients receive a treatment, the K-M plot also shows the survival rate of the patients in response to the treatment. As the time progresses, some patients may experience death, and the survival rate decreases. Some other patients can be censored (dropped) from the plot due to other events not related to the studied event, and those unrelated events are represented by ticks in the K-M plot. The length of each horizontal line represents the survival duration for that interval, and all survival estimates to a given point represent the cumulative probability of surviving to that time.

In FIG. 1A, chart 100 includes two K-M plots of the survival rates of different cohorts A and B of patients. Cohorts A and B can include, for example, cohorts of patients having different characteristics, receiving different treatments, etc. From FIG. 1A, the median survival (50% of patients would be estimated to be surviving) in cohort A is about 11 months, but is about 6.5 months in cohort B. In addition, the percentage of surviving patients, indicated by the horizontal lines of the plots, can also provide a prediction of a survival rate of a patient in the cohort with respect to time. For example, at 4 months from the diagnosis, a patient in cohort A has a survival rate of about 70% (0.7), whereas a patient in cohort B has a survival rate of about 30% (0.3).

While population-based survival statistics are available across a wide range of cancer types and patients, patient-specific information can be harder to discern. Specifically, while the overall five-year survival of patients with stage IV colon cancer is relatively low (e.g., about 14% according to Surveillance, Epidemiology, and End Results (SEER) statistics of National Cancer Institute (NCI)), some individual patients will have a considerably better than average survival. The critical question for an oncologist then, when seeing an individual patient, is not the population survival but what the individual patient's survival rate prediction is.

FIG. 1B illustrates example applications of survival rate prediction for a patient. As shown in FIG. 1B, data 102 representing a survival rate prediction of a patient, such as a K-M plot of FIG. 1A, can be input to a clinical decision support tool 104. Data 102 can include the survival rate prediction of the patient without treatment and/or survival rate predictions of the patients for different treatments.

Clinical decision support tool 104 can generate various information to assist a clinician in administering care/treatment to the patient based on data 102. For example, to facilitate care to the patient, clinical decision support tool 104 can generate information 106 to allow the clinician to better assess the patient's prognosis, such as comparison between the patient's predicted survival rates with other patients, the patient's life expectancy, etc. Information 106 can facilitate discussions between the clinician and the patient regarding the patient's prognosis as well as assessment of treatment options and the patient's planning of life events. As an illustrative example, if clinical decision support tool 104 predicts that the patient has a relatively long remaining life (e.g., 5 years), the patient may decide to undergo an aggressive treatment that is more physically demanding and has more serious side effects. But if clinical decision support tool 104 indicates that the patient has a relatively short remaining life (e.g., less than a year), the patient may decide to forgo the treatment or to undergo an alternative treatment, and plan for care and life events in the remainder of the patient's life.

In addition, in a case where data 102 contains survival rate predictions of the patient for different treatments, clinical decision support tool 104 can also output information 108 to facilitate a selection of optimal treatment for the patient. For example, clinical decision support tool 104 can display different K-M plots of the patient for different treatments based on data 102. The clinician can then select a treatment to, for example, maximize the survival rate of the patient at a given time, to maximize the expected remaining life of the patient, etc.

II. Clinical Prediction Using Machine Learning Models

A machine learning predictive model can be trained to perform a clinical prediction for a patient based on a patient data comprising a set data categories. A machine learning predictive model can be a very powerful tool for performing a clinical prediction, since the model can expose hidden relationships between a clinical parameter to be predicted (e.g., a survival rate) and various data categories of patient data that are otherwise not considered by the clinician. The machine learning model can be trained using the data of a very large population of patients to learn various relationship between the clinical parameter and the various data categories, and then perform a prediction for a patient based on the patient data and the relationships the model has learnt through training.

Figure 2A:
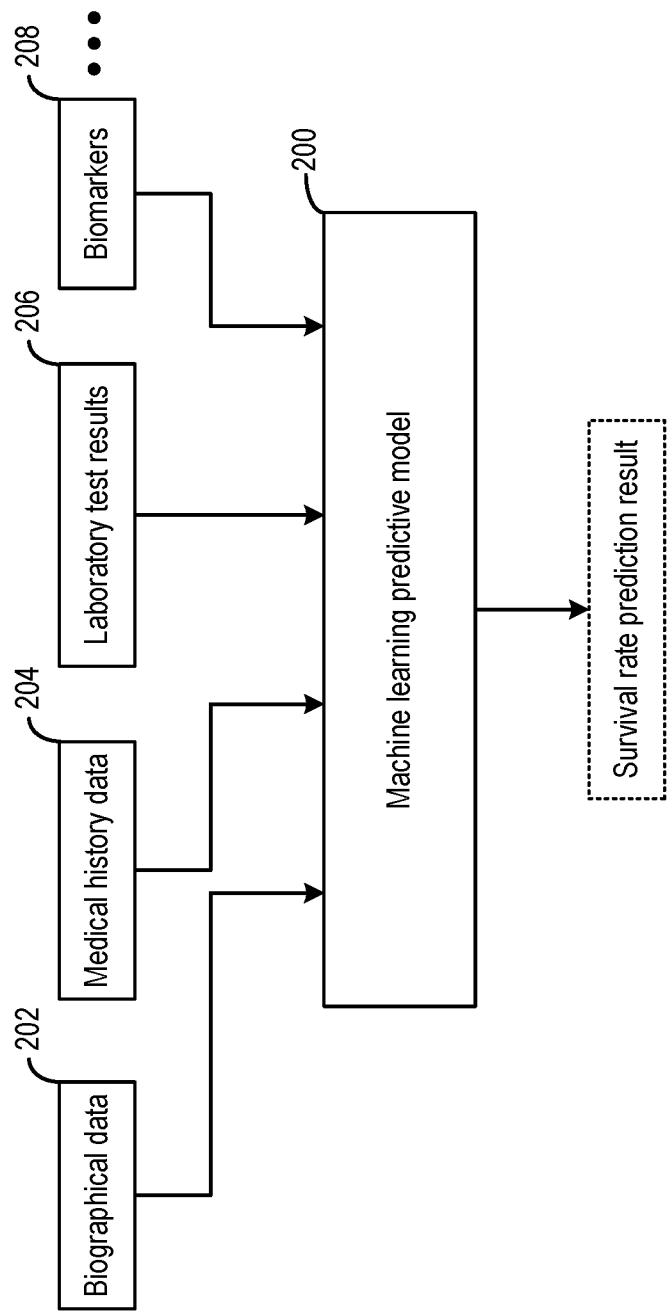

FIG. 2A illustrates an example of using a machine learning model to perform a prediction of survival rate of a patient at a pre-determined time after diagnosis of a cancer. As shown in FIG. 2A, a machine learning predictive model 200 can receive, as inputs, various types of data of a patient including, for example, biographical data 202, medical history data 204, laboratory test results 206, biomarkers data 208, etc., and generate a prediction result 210 of a survival rate of the patient based on the inputs. The survival rate can provide a likelihood that the patient survives at a pre-determined time (e.g., 500 days, 1000 days, 1500 days, etc.) after the patient is diagnosed of a medical condition (e.g., an advanced stage cancer). The survival rates with respect to time can be used to generate a patient-specific Kaplan-Meier (KM) plot for the patient.

FIG. 2B illustrates a table 220 which provides examples of categories of biography data 202, medical history data 204, laboratory test results 206, and biomarkers 208. As examples, biographical data 202 can include various categories of information, such as age, gender, race, etc. As examples, history data 204 can include various categories of information, such as a diagnosis result (e.g., a stage of cancer, a site of colorectal cancer (CRC), etc.), a habit of the patient (e.g., whether the patient smokes), treatment history of the patient (e.g., which treatment(s) the patient has received), etc.

As examples, laboratory test results 206 can include different categories of laboratory test results of the patient, such as a leukocytes count, a hemoglobin count, a platelets count, a hematocrit count, an erythrocyte count, a creatinine count, a lymphocytes count, measurements of protein, bilirubin, calcium, sodium, potassium, alkaline phosphatase, carbon dioxide, monocytes, chloride, lactate dehydrogenase, glucose, etc.

As examples, biomarker data 208 can include measurements of various biomarkers for different cancer types, such as estrogen receptor (ER), progesterone receptor (PR), human epidermal growth factor receptor 2 (HER2), epidermal growth factor receptor (EGFR, or HER1) for breast cancer, ALK (anaplastic lymphoma kinase) for lung cancer, KRAS gene for lung and colorectal cancers, BRAF gene for colorectal cancer, etc. It is understood that other categories of clinical data not shown in FIG. 2B, such as biopsy image feature data, can also be input to machine learning prediction model 200 to perform the clinical prediction.

A. Random Forest

Figure 2C:
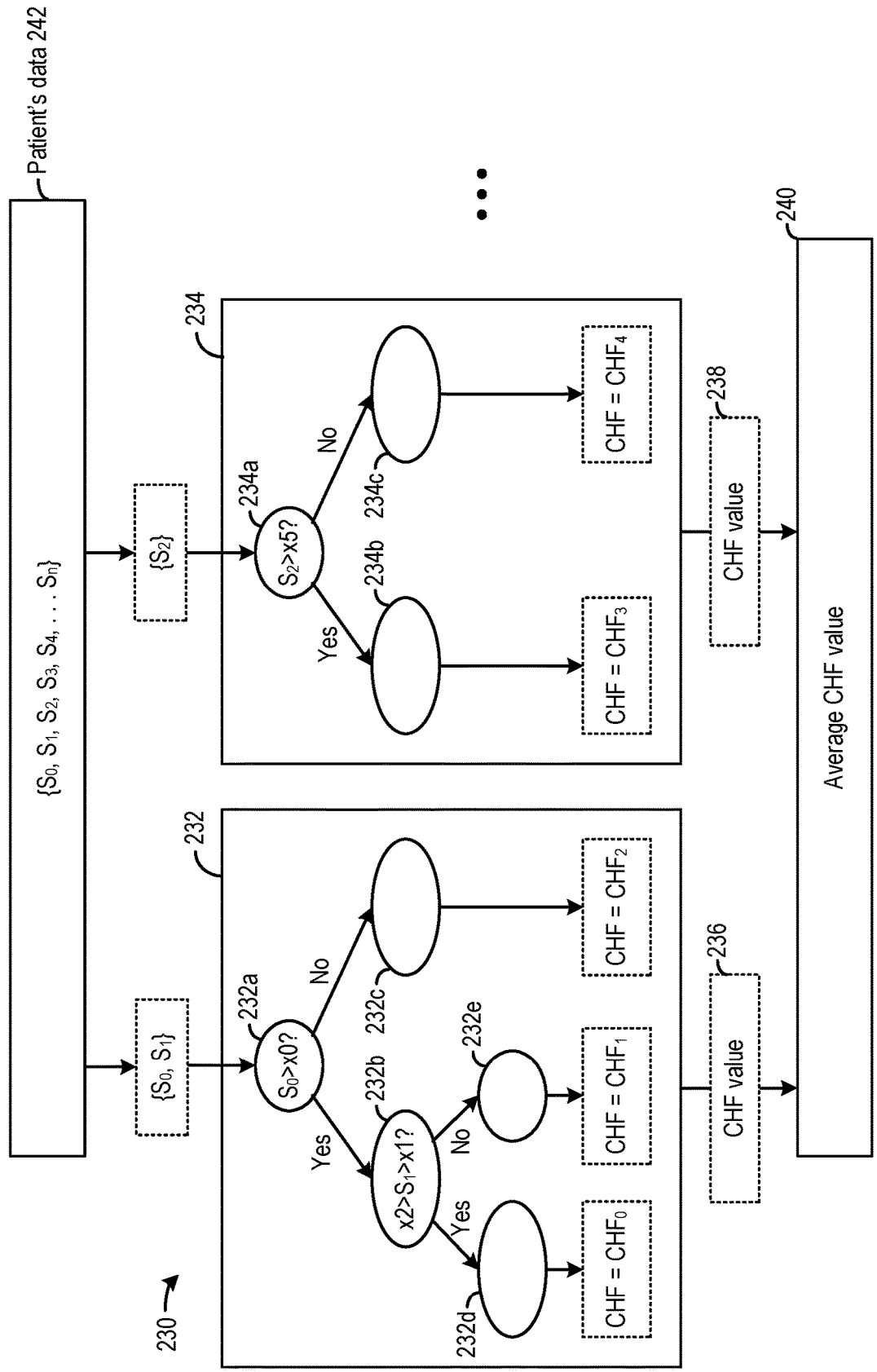

Machine learning prediction model 200 can be implemented using various techniques, such as a random forest tree, a regression model, etc. FIG. 2C illustrates an example of a random forest model 230 that can be used to implement machine learning prediction model 200. As shown in FIG. 2C, random forest model 230 can include a plurality of decision trees including, for example, decision trees 232 and 234. Each decision tree can include multiple nodes including a root node (e.g., root node 232a of decision tree 232, root node 234a of decision tree 234, etc.), and child nodes (e.g., child nodes 232b, 232c, 232d, and 232e of decision tree 232, child nodes 234b and 234c of decision tree 234, etc.). Each parent node that has child nodes (e.g., nodes 232a, 232b and 234a) can be associated with pre-determined classification criteria to classify a patient into one of its child nodes. Child nodes that do not have child nodes are terminal nodes, which include nodes 232d and 232e (of decision tree 232) and nodes 234b and 234c (of decision tree 234), are each assigned a value of a cumulative hazard function (CHF).

The value of CHF can represent the risk of death (or a survival rate) at a particular time. CHF represents the sum of a hazard function h(t), which represents the instantaneous risk of death at a particular time t, and therefore CHF itself is also a function of time. Each decision tree can classify the patient into one of the terminal node and outputs a CHF value, such as CHF value 236 from decision tree 232 and CHF value 238 from decision tree 234. The CHF values for a patient from each of the individual decision trees can be averaged to generate an overall CHF value 240 ($CHF_{combine}$) for the patient to represent the patient's survival rate at a particular time t. The random forest model 230 shown in FIG. 2C can be trained to predict a CHF value for a particular time, and multiple random forest models 230 can be used to predict the overall CHF value 240 for a patient for different times.

The survival rate m(t) of the patient at time t can be calculated based on an exponential function (exp) of the combined cumulative hazard function $CHF_{combine}$, according to the following equation:

$$m(t)=\exp(-CHF_{combine}(t)) \quad \text{(Equation 1)}$$

Each decision tree can be assigned to process different subsets of the data categories of patient data to generate the CHF value. For example, as shown in FIG. 2C, patient data 242 include a set of data categories $\{S_0, S_1, S_2, S_3, S_4, \ldots S_n\}$. Decision tree 232 can be assigned and trained to process data categories $S_0$ and $S_1$, and decision tree 234 can be assigned and trained to process data category $S_2$, while other decision trees can be assigned to process other subsets of data categories.

A parent node in a decision tree can then compare a subset of patient data 242 corresponding to one or more of the assigned data categories against one or more thresholds to classify the patient into one of its child nodes. Specifically, referring to decision tree 232, root node 232a can classify the patient into child node 232b if the patient data of data category $S_0$ exceeds a threshold x0, and into terminal node 232c if otherwise. Child nodes 232b can further classify the parent into one of terminal nodes 232d or 232c based on that patient data of data category $S_1$. Depending on which terminal node the patient is classified into based on data categories $S_0$ and $S_1$, decision tree 232 can output a CHF value of $CHF_0$, $CHF_1$ or $CHF_2$. Moreover, decision tree 234 can also output a CHF value of $CHF_3$ or $CHF_4$ depending on which terminal node the patient is classified into based on data category $S_2$.

Each decision tree in a random forest model can be generated in a training process over patient data of a set of data categories, as well as survival statistics, of a large population of patients. In addition, the training process can determine the subsets of data categories assigned to each decision tree, the classification criteria at each parent node of the decision trees, as well as the value of the cumulative hazard function at each terminal node. Specifically, the training process can start with randomly assigning a subset of the data categories to a root node of a decision tree, and different subsets of the data categories can be assigned to the root nodes of different decision trees. The process of generating trees can be repeated until a target number of decision trees, which can be defined by hyperparameters of the training process, is reached. Moreover, in a bagging process, the root node of a decision tree can be assigned to a random set of samples of the patient data of the assigned subset of the data categories to perform the training.

As part of the training process, the root node (and each parent node thereafter) can be split into child nodes in a recursive node-splitting process based on the random set of samples of the patient data assigned to the root node. In the node-splitting process, a node representing a set of patients can be split into two child nodes each representing a subset of the patient based on thresholds for the subset of the data categories, with the subset of data categories and thresholds selected to maximize a difference in the number of surviving patients/deaths between the two child nodes, such that patients represented in two child nodes have as similar survival statistics as possible. For example, referring to decision tree 232, during the training process, it can be determined that by dividing the random samples of patients data assigned to decision tree 232 into two groups based on the data category $S_0$ and threshold x0, the difference between the numbers of surviving patients in the two groups can be maximized versus other classification criteria (e.g., based on data category S1, setting a different threshold for $S_0$, etc.).

The process can then be repeated on the child nodes to generate additional child nodes until, for example, a threshold minimum number of deaths/non-survival patients is reached in a particular child node, which can then become a terminal node. For example, among the patients classified into terminal nodes 232c, 232d, and 232e, the number of deaths/non-survival patients reaches the threshold minimum number, therefore the root-splitting operation stops at those nodes. The cumulative hazard function output at each of these terminal nodes can be represented by a percentage of the surviving patients classified into the terminal node at a given time. For example, for 20 patients classified into terminal node 232c, a hazard function can be computed based on a number of the patients surviving and not surviving at different times until a particular time (e.g., 4 days) is reached. The CHF value at that particular time can then be generated based on summing the hazard functions for that particular time. The training can be repeated based on the survival statistics of the patients at different times to generate different decision trees and different thresholds for classifying patients into different child nodes, so that different CHF values can be predicted as a function of time.

B. Mathematical Model

Figure 2D:
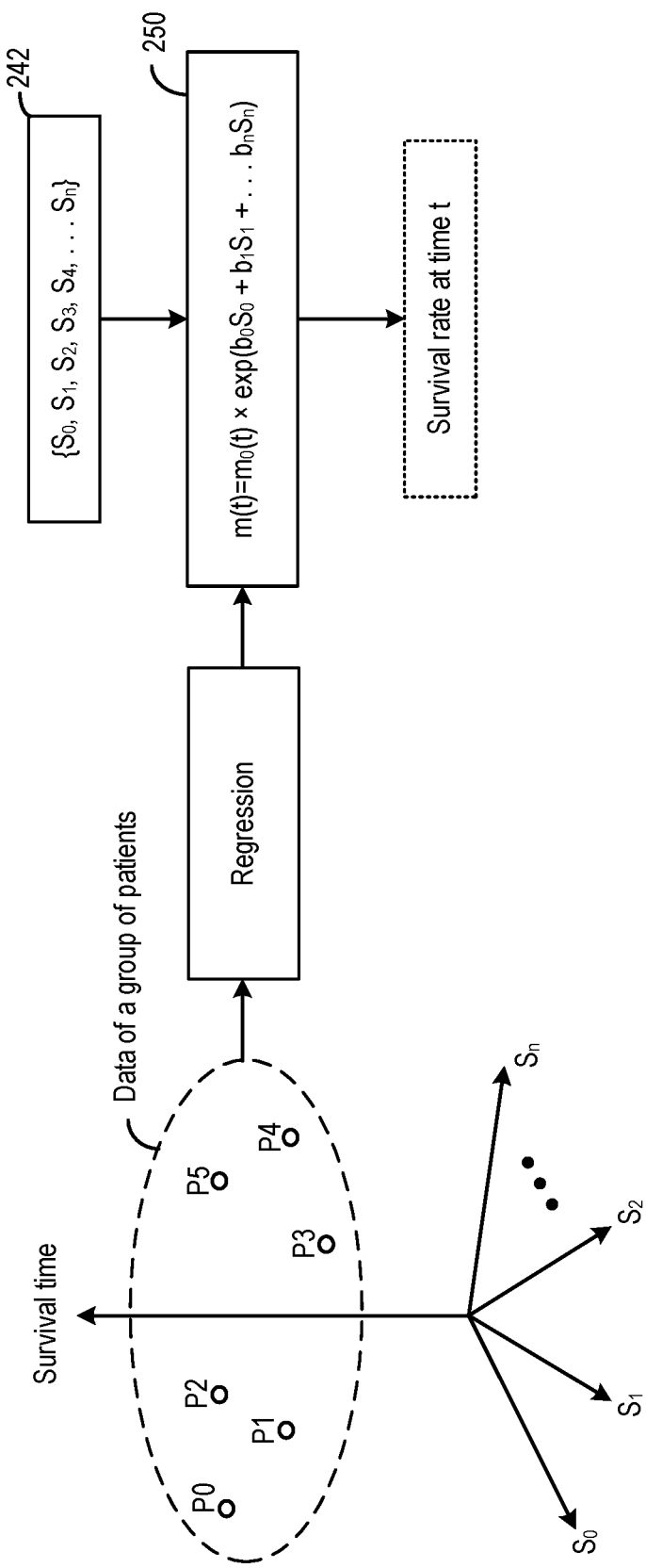

In addition to random forest model 230, a regression model can also be used to predict the survival rate of a patient as a function of time. FIG. 2D illustrates an example of a regression model 250. As shown in FIG. 2D, regression model 250 can be a Cox proportional hazards model to predict the survival rate of a patient. A survival rate function m(t) can be represented by the following equation:

$$m(t)=m_0(t) \times (b_0 S_0 + b_1 S_1 + \ldots + b_n S_n) \quad \text{(Equation 2)}$$

In Equation 2, $m_0(t)$ can represent a base hazard, which can be calculated empirically using the actual survival data of the patients and censoring and is a function of time t. For example, if 20 patients are known to be alive on day 9 and one of the 20 dies, the base hazard at day 9 would be 0.05 (1/20). Patients lost to follow up or still alive at the study end are censored and thus removed from both the numerator and denominator at all time points past the time of censoring. For example, if a patient was alive on day 1400 when the study ended, that patient would be excluded from the numerator and denominator in the hazard calculation for all days after day 1400. The survival rate of a patient can be determined based on multiplying the base hazard with a linear function of a set of variables each representing a data category, such as $S_0$, $S_1$, $S_n$, etc. Each variable can be scaled by a corresponding coefficient in the linear function. For example, the variable of data category $S_0$ can be scaled by a corresponding coefficient $b_0$, the variable of data category $S_1$ can be scaled by a corresponding coefficient $b_1$, etc. Each coefficient can reflect the impact of the data category on the risk of death. Survival rate function M(t) can indicate the risk of death changes (increases) with time as indicated in the K-M plot.

The coefficients of regression model 250 can also be determined in a training process that includes fitting of the mathematical model over patient data of the different data categories, as well as survival statistics, of a large population of patients based on regression. For example, based on the survival times of the patients (represented by P0, P1, P2, etc. in FIG. 2D), a K-M plot of a percentage of the surviving patients in the group (with the group size adjusted with respect to time to account for deaths) at different times can be determined to represent the target survival rates at the different times. The target survival rates can be represented by the base hazard $m_0(t)$ computed from a group of patients including patients P0, P1, P2, etc. The coefficients can then be determined based on the values of the patients for the different data categories at different times, to fit the output of regression model 250 with the target survival rates.

III. Clinical Prediction Using a Single Machine Learning Model

Although a machine learning predictive model can be very powerful in performing a clinical prediction and in assisting a clinician in generating a clinical decision, key challenges have limited the introduction of machine learning-based predictive models into real clinical settings. One set of challenges relates to inter-patient variability in data availability. In most real world datasets, many patients will lack recorded findings for many data categories. On the other hand, a machine learning model is typically trained using data of a large set of data categories to expose more hidden links between the parameter to be predicted and the large set of data categories. For example, random forest model 230 and regression model 250 may be trained based on a large number of data categories from those listed in table 220. If the machine learning model is trained to make a prediction based on a set of data categories, but a patient data lack one or more categories from the set, the machine learning model may be unable to perform a prediction based on the patient data.

The data categories included in the data of a group of patients can vary among different patients due to various reasons, which leads to large data heterogeneity. For example, some hospitals may have a laboratory test menu that includes more than 1,000 unique orderable tests. Depending on the patients' situation (e.g., clinical setting, age, gender, economic condition, etc.), most patients will have had at most a small fraction of these possible tests, and the patients may have different fractions of these tests due to their different situations. As another example, different patients may lack different categories of non-laboratory clinical data, including other diagnostic studies, elements of patient history, biopsy data, etc. The issue of data heterogeneity becomes particularly significant when considering time series data; even patients who have similar diagnostic tests or physical exam maneuvers performed may have them at different time points or repeated at varying intervals. In all these cases, due to the various missing data categories in the patients' data, the machine learning model may be unable to perform a prediction for a large number of patients, which limits the utility of the machine learning model.

One approach to overcome the challenges posed by data heterogeneity to machine learning model is by an imputation process, in which a set of clinical data of a patient can be pre-processed to create additional clinical data elements for the missing data categories, so that the patient data, including the original and imputed clinical data elements, can include the full set of data categories as input to the machine learning model. The imputation process can estimate a distribution or value of each data element of the missing data categories, based on the original patient data. The imputation process, however, can have major limitations. Specifically, most imputation algorithms assume data are "missing at random" (MAR), but the MAR assumption is typically not valid for most clinical data. This is because the diagnostic studies that generate the clinical data are selected and ordered in response to the clinical setting, not by random, therefore the presence (or absence) of a certain data category in a patient data is also not random. Moreover, imputation can introduce additional uncertainty and inaccuracy into predictions and may obscure some of the hidden relationship between the predicted parameter and the data categories.

IV. Clinical Prediction Using a Meta-Model of Machine Learning Models

A machine learning, such as a random forest decision tree model (as shown in FIG. 2C) and a regression model (as shown in FIG. 2D), can be trained using a large number of data categories representing different features of patients, to improve the accuracy of prediction. But a patient's data typically does not have all these data categories. Imputing the missing data categories allows the machine learning model to be used to make a prediction for the patient, but such arrangements can introduce error and uncertainty, as explained above.

Disclosed herein are techniques for performing a clinical prediction using a combined learning model (herein after, a "meta-model") comprising a plurality of machine learning models, to address some of the issues above. Each of the plurality of machine learning models in the meta-model is separately trained using data of a set of data categories and assigned a weight that indicate the performance of the machine learning model. To perform a prediction for a patient, machine learning models being trained with the data categories present in the patient's data can be selected to generate prediction results. The prediction results can be combined based on the weights of the selected machine learning models to generate a combined prediction result for the patient.

A. Meta-Model

Figure 3A:
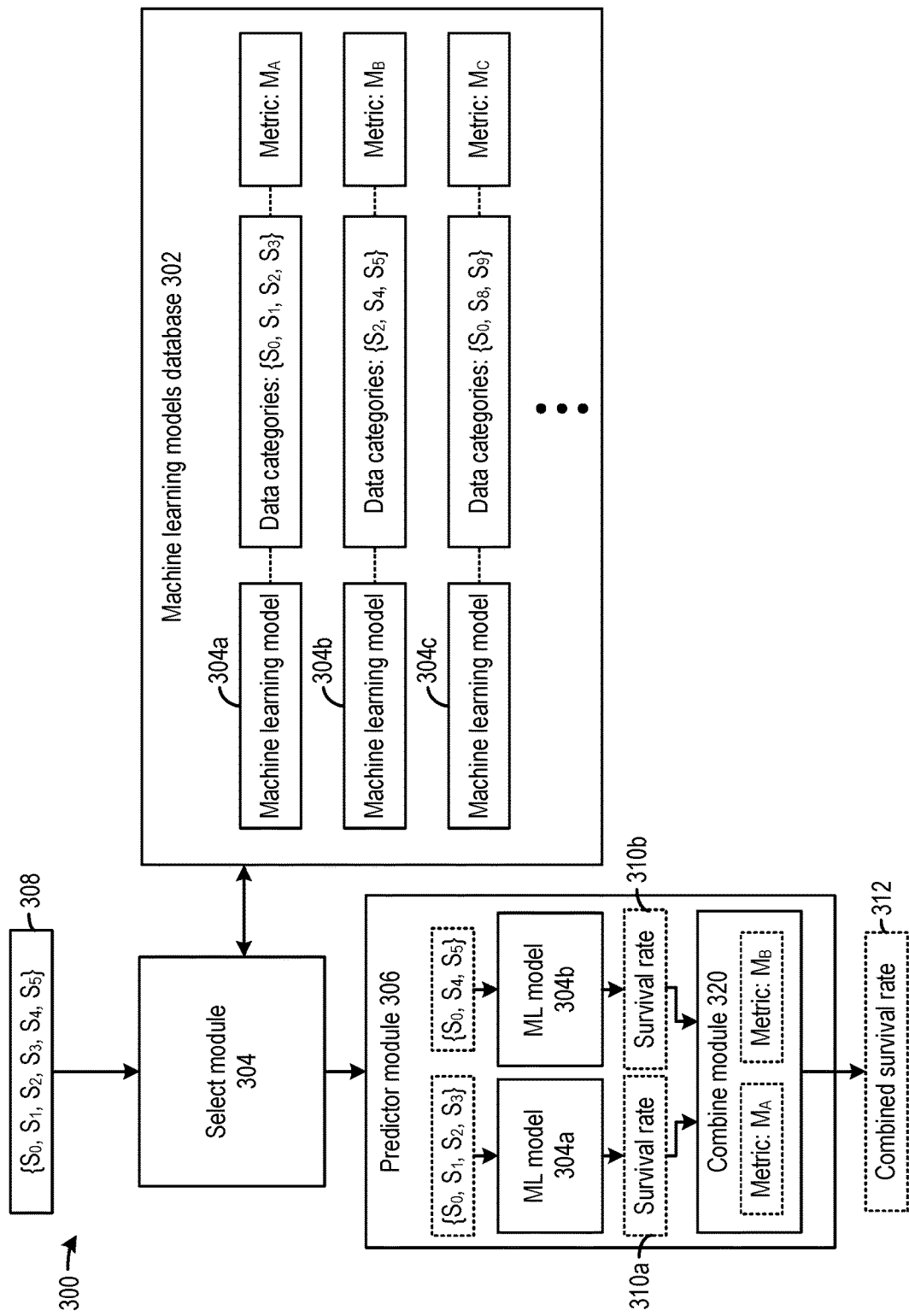
FIG. 3A, FIG. 3B, FIG. 3C, and FIG. 3D illustrate examples of performing clinical predictions using a meta-model, according to certain aspects of this disclosure.
Figure 3B:
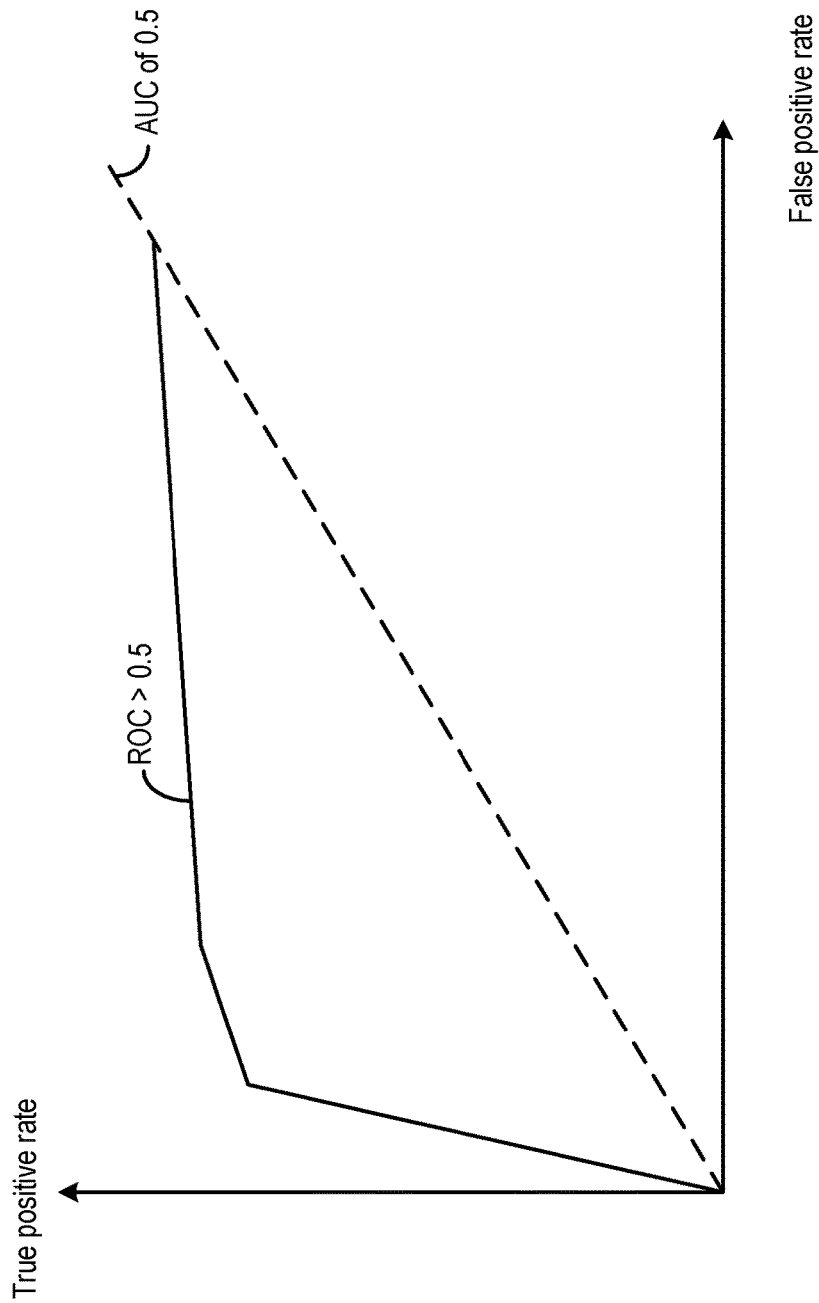
Figure 3C:
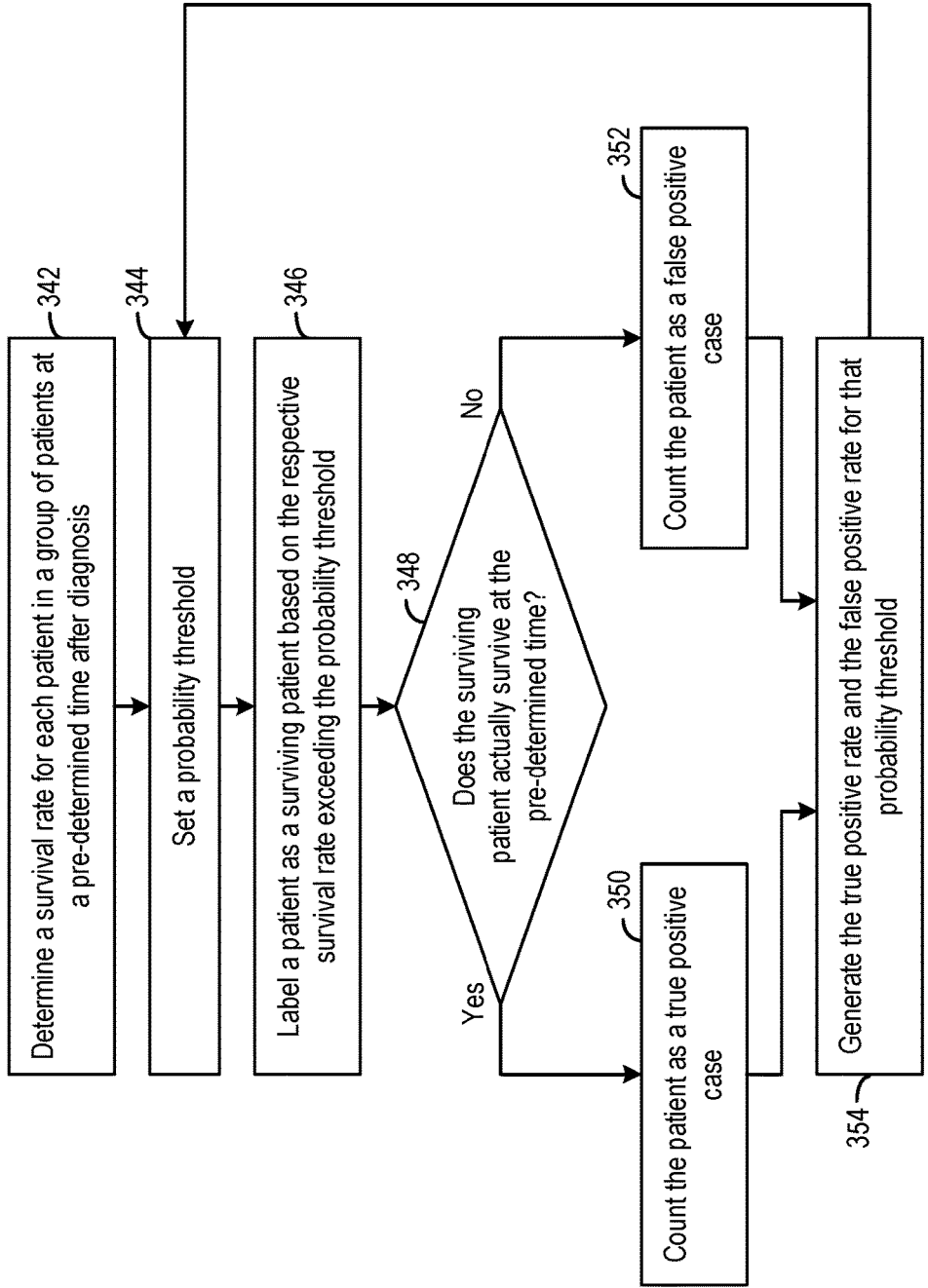

FIG. 3A, FIG. 3B, and FIG. 3C illustrate examples of a clinical prediction system 300 which can address at least some of the issues described above. As shown in FIG. 3A, clinical prediction system 300 comprises a machine learning models database 302, a select module 304, and a predictor module 306. In some examples, various modules of clinical prediction system 300, including select module 304 and predictor module 306, can be implemented as software instructions executable by a hardware processor, to perform the functions described below.

Select module 304 can accept data 308 of a patient as input. Based on the data categories included in data 308, select module 304 can select a plurality of machine learning models from machine learning models database 302 to form a meta-model, and provide the meta-model to predictor module 306. Predictor module 306 can then use the machine learning models included in the meta-model to process data 308 to generate prediction outputs for the patient, such as survival rates 310a and 310b, and combine the prediction outputs from the machine learning models to generate a combined prediction output, such as a combined survival rate 312 of the patient. A clinical prediction (e.g., a survival rate of the patient as a function of time and/or treatment, the expected remaining life of the patient, etc.) can then be made based on the combined prediction output.

Specifically, machine learning models database 302 may store a plurality of machine learning models including model 304a, 304b, 304c, etc. Each machine learning model can include, for example, a random forest model (e.g., random forest model 230 of FIG. 2C), a mathematical model (e.g., regression model 250 of FIG. 2D), or other types of machine learning models, to perform a prediction (e.g., survival rate). The random forest model and the mathematical model can include a set of sub-models each associated with a respective time, thereby generating different survival rates for different times. Each machine learning model in machine learning model database 302 is separately trained using data of a set of data categories to perform the prediction, and different machine learning models are trained using data of different sets of data categories, although there can be overlapping data categories among the different sets. For example, machine learning model 304a is trained using a set of data categories $S_0$, $S_1$, $S_2$, and $S_3$. Moreover, machine learning model 304b is trained using a set of data categories $S_2$, $S_4$, and $S_5$. Further, machine learning model 304c is trained using a set of data categories $S_0$, $S_8$, and $S_9$. Machine learning models database 302 can also include other machine learning models which are trained using a subset of data categories used to train machine learning models 304a-304c. For example, machine learning models database 302 can include a machine learning model trained using data categories $S_4$, and $S_5$.

In addition, each of the plurality of machine learning models can be associated with a performance metric. The performance metric can indicate a degree of confidence that a particular machine learning model generates a correct prediction. For example, machine learning model 304a can be associated with a performance metric value $M_A$, machine learning model 304b can be associated with a performance metric value $M_B$, whereas learning model 304c can be associated with a performance metric value $M_C$. As to be described below, the performance metric values can be obtained from a validation process after the machine learning models are trained.

To perform a prediction for the patient based on data 308, select module 308 can perform, in machine learning models database 302, a search of machine learning models that accept a subset (or the entirety) of data categories present in data 308. In one example, select module 308 can obtain the requisite data categories of each and every machine learning model in the database (e.g., data categories $S_0$, $S_1$, $S_2$, and $S_3$ for machine learning model 304a, data categories $S_2$, $S_4$, and $S_5$ for machine learning model 304b, etc.), compare the data categories with those of data 308, and determine whether the requisite data categories of a machine learning model represent a subset (or the entirety) of the data categories in data 308. If they are, select module 308 can select the machine learning model to form the meta-model. Select module 308 can then provide the selected machine learning models to predictor module 306. In the example of FIG. 3A, data 308 include data categories $S_0$, $S_1$, $S_2$, $S_3$, $S_4$, and $S_5$. Based on the presence of these data categories in data 308, select module 304 can select machine learning model 304a, which is trained using data of data categories $S_0$, $S_1$, $S_2$, and $S_3$ included in data 308, as well as machine learning model 304b, which is trained using data of data categories $S_2$, $S_4$, and $S_5$ included in data 308 to be part of the meta-model, as well as other machine learning model(s) trained using any subset of data categories $S_0$, $S_1$, $S_2$, $S_3$, $S_4$, and $S_5$. On the other hand, select module 304 does not select machine learning model 304c since the model is trained using data of data categories $S_0$, $S_8$, and $S_9$, and data categories $S_5$, and $S_9$ are not present in data 308. Select module 304 can then fetch machine learning models 304a and 304b, as well as their associated metrics $M_A$ and $M_B$, to predictor module 306.

Predictor module 306 can use machine learning models 304a and 304b fetched by select module 304 to perform a prediction. Predictor module 306 can input a first subset of data 308 corresponding to data categories $S_0$, $S_1$, $S_2$, and $S_3$ to machine learning model 304a to generate survival rate 310a. Predictor module 306 can also input a second subset of data 308 corresponding to data categories $S_0$, $S_4$, and $S_5$ to machine learning model 304b to generate survival rate 310b.

Predictor module 306 further includes a combine module 320 to combine survival rates 310a and 310b to generate combined survival rate 312 based on performance metrics $M_A$ and $M_B$. In one example, combine module 320 can associate a weight for each survival rate based on the performance metric of the machine learning model that generates the survival rate, and then generate combined survival rate 312 based on a weighted average of the survival rates, in which each survival rate can be scaled by the associated weight. The weight can be generated to reflect a confidence level in the prediction of the survival rate by the machine learning model, as reflected by the performance metric. For example, a larger weight can be assigned to a survival rate from a machine learning model having a higher confidence level, while a lower weight can be assigned to a survival rate from a machine learning model having a lower confidence level. Combined survival rate 312 can then be provided to a clinical decision support tool, such as clinical decision support tool 104, to generate various information to support a clinical decision, as described above.

B. Performance Metric

As described above, each of the plurality of machine learning models in machine learning models database 302 can be associated with a performance metric, which can be used to generate the combined output of the meta-model. The performance metric can indicate a degree of confidence that a particular machine learning model generates a correct prediction. The performance metric of a machine learning model can be determined using various techniques, such as determining the area under the receiver operating characteristic (ROC) curve of the machine learning model.

FIG. 3B illustrates an example of a ROC curve 330 of a machine learning prediction model. As shown in FIG. 3B, ROC curve 330 provides a plot between corresponding true positive rates and the false positive rates of the machine learning model in performing a prediction. The true positive rate refers to the rate at which the machine learning model correctly predicts an event happens, whereas the false positive rate refers to the rate at which the machine learning model predicts an event happens but the event does not happen. A value of 0.5 for the area under curve (AUC) of ROC, as represented by the dotted line, meaning that the true positive rate and the false positive rate are equal, means the machine learning model cannot discriminate and is undesirable, while a larger AUC exceeding 0.5, represented by the solid line, can indicate a higher of confidence in the prediction. A weight can be assigned to a machine learning model based on the AUC of the ROC of the machine learning model, with a larger weight assigned to a machine learning model having a larger AUC of the ROC and vice versa.

In a case where the machine learning models are trained to output a survival rate of a patient, the definition of true positive and false positive can be based on various definitions. In one example, a true positive case can be defined as the machine learning model outputting that the survival probability of the patient, at a given time, exceeds a probability threshold and the patient actually surviving at that given time, whereas a false positive case can be defined as the survival probability of the patient exceeding the probability threshold but the patient not surviving at that given time. In another example, a true negative case can also be defined as the machine learning model outputting that the survival probability of the patient, at a given time, falling below a probability threshold and the patient actually not surviving at that given time, whereas a false negative case can be defined as the survival probability of the patient falling below the probability threshold but the patient actually surviving at that given time.

FIG. 3C illustrates a validation process 340 to generate the weight (e.g., $M_A$, $M_B$, etc.) of a machine learning model in FIG. 3A. In this example, the machine learning model has been trained to predict a survival rate of a patient at a pre-determined time after a diagnosis.

At step 342, data of a group of patients whose survival statistics at the pre-determined time are known, can be input to the machine learning model to predict a survival rate of each patient in the group. The data corresponds to the categories for which the machine learning model has been trained.

At step 344, a probability threshold is set. The probability threshold can be selected from one of a set of probability thresholds used to test the machine learning model. For example, the set of probability thresholds may include a set of discrete values including 0.2, 0.4, 0.6, and 0.8, and the probability threshold can be selected from the set. Finer or coarser gradations may be used. And the differences between the values does not have to be uniform.

At step 346, each patient in the group can be labelled as either surviving or not-surviving based on comparing the predicted survival rate of the patient against the probability threshold. Specifically, if the predicted survival rate is higher than the probability threshold, the patient can be labelled as a surviving patient, whereas if the predicted survival rate is lower than the probability threshold, the patient can be labelled as a non-surviving/deceased patient.

At step 348, for each patient labelled as surviving, a determination is made about whether that patient actually survives at the pre-determined time based on the survival statistics. If the patient is labelled as surviving and actually survives at the pre-determined time, the patient can be counted as a true positive case, in step 350. On the other hand, if the patient is labelled as surviving but does not survive at the pre-determined time, the patient can be counted as a false positive case, in step 352.

At step 354, the true positive rate and the false positive rate for that probability threshold can be generated. The true positive rate can be generated by determining a percentage of the true positive cases out of the number of patients represented in the data, whereas the false positive rate can be generated by determining a percentage of the false positive cases out of the number of patients represented in the data.

Following step 354, steps 344-352 can then be repeated for a different probability threshold selected from the set of probability thresholds. As such, a pair of false positive rate and true positive rate can be obtained for different probability thresholds, and the corresponding pairs of false positive rate and true positive rate can be plotted to generate an ROC for the machine learning model.

Validation process 340 can be performed for each machine learning model in machine learning models database 302 to determine the area under curve (AUC) of the ROC of each model. The weight of each model can be determined based on the AUC of the respective ROC based on the following equation:

$$\text{weight} = (\text{AUC} - 0.5)^n \quad \text{(Equation 3)}$$

In Equation 2, the weight of a model can be based on a difference between the AUC and 0.5. As explained above, 0.5 refers to a case where the true positive and true negative rates are the same, which means the machine learning model output is completely random and does not discriminate, and the weight of such a model should be close to zero. On the other hand, an AUC larger than 0.5 means the model can discriminate, and a larger AUC reflects a higher confidence level, therefore the weight can increase with the AUC. The difference between AUC and 0.5 can be raised to a power n larger than or smaller than one to emphasize (or deemphasize) the influence of AUC on the weight. The value of n can be determined to, for example, maximize the AUC of the meta-model. For example, as part of the validation process, the AUC of the ROC of the meta-model's combined survival rate output, based on weighted average of the survival rate output of the machine learning models included in the meta-model, can be determined for different values of n. The value of n that maximizes the AUC of the ROC of the meta-model can then be determined and included in the computation of weights, when the meta-model is used to compute the combined survival rate of a new patient.

In addition to AUC, the weights of the machine learning models can be determined based on other performance metrics, such as Harrell's C-index (also known as concordance index). To determine a Harrell's C-index for a machine learning model, the model can be used to compute the survival rate of a group of patients whose survival times are known. Concordant pairs and discordant pairs of patients can be identified. A concordant pair of patients refers to a pair of patients in which a first patient is predicted to have a higher survival rate than a second patient and the first patient has a longer survival time than the second patient. A discordant pair of patients refers to a pair of patients in which a first patient is predicted to have a higher survival rate than a second patient, but the first patient has a shorter survival time than the second patient. The Harrell's C-index for the machine learning model can be determined as follows:

$$C-\text{index} = \frac{\text{Number of concordant pairs}}{\text{Number of concordant pairs} + \text{Number of discordant pairs}} \quad \text{(Equation 4)}$$

A larger weight can be assigned to a machine learning model having a larger C-index, and vice versa.

In the machine learning models of this disclosure, the concordance between two patients can in part be a function of time, the definition of concordance can be adapted to accommodate this time dependency. In one example, a pair of patients at a given time point for which one patient is known to be alive and the other deceased, can be defined as "concordant" if the patient who is alive has a higher predicted probability of survival at the time point and "discordant" if the deceased patient has a higher predicted probability of survival at the time point. In some examples, the concordance/discordance within a group of patients can be defined using a bootstrap approach in which random pairs of patients at different time points are sampled, and concordant and discordant bootstrap replicates are counted, while replicates representing patient-pair-time point combinations in which the patients are both known to be alive, deceased, or either or both patients have an unknown survival status (e.g. who would be censored from the K-M plot) are discarded from the counts.

C. Training and Validation of Machine Learning Models

Figure 3D:
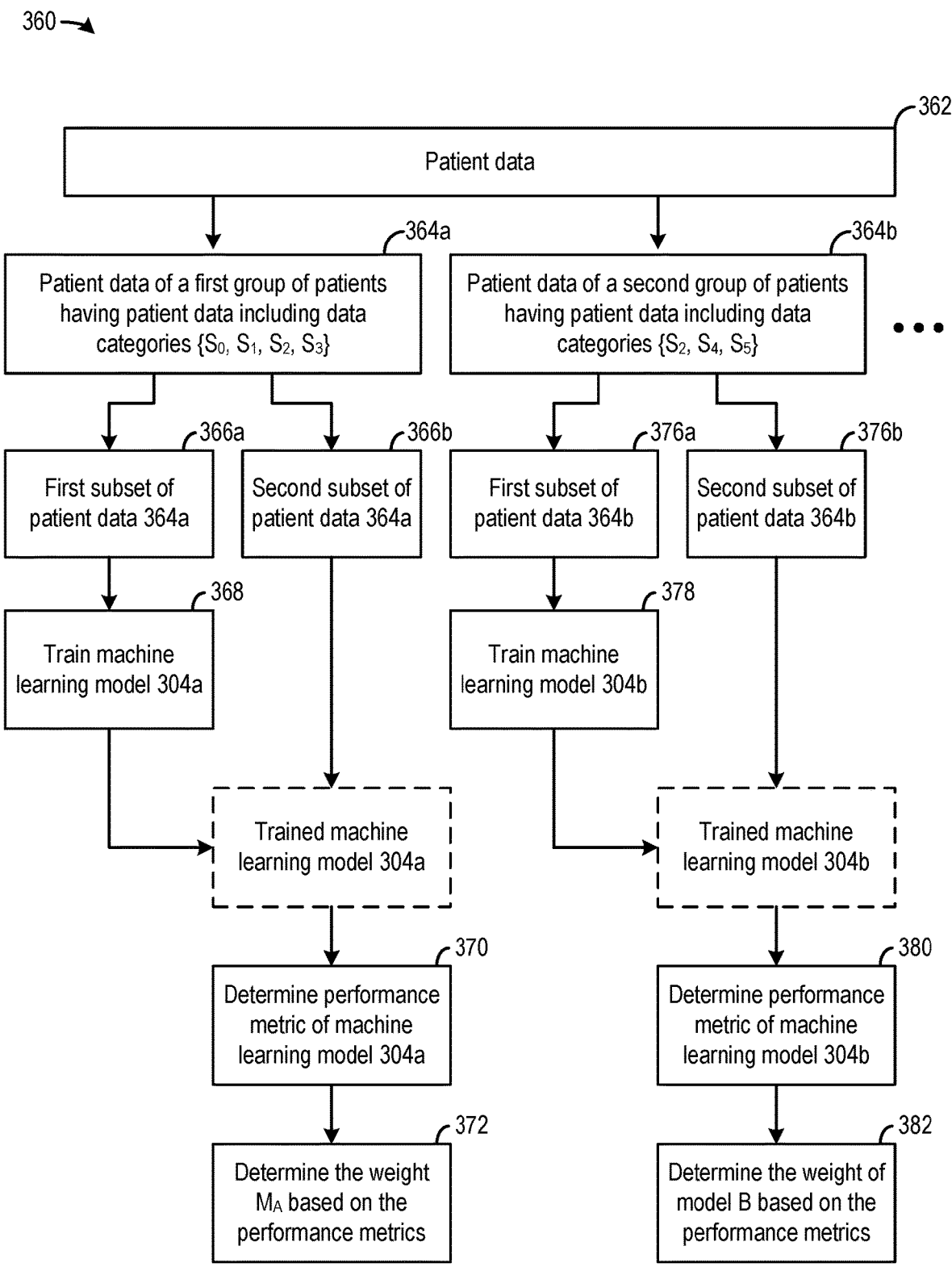

In some examples, the training of each machine model in machine learning models database 302, as well as the determination of performance metric of each machine model, can be performed based on different subsets of patient data of the same group of patients in a cross-validation process. FIG. 3D illustrates an example of the training process 360 of the machine learning models of machine learning models database 302 including machine learning models 304a, 304b, etc.

As shown in FIG. 3D, training process 360 can receive training data 362 as input. Training data 362 can include patient data of a large population of patients. The data categories included in the patient data may vary between different patients. Patient data of a group of patients having the requisite data categories for a machine learning model can be identified for each machine learning model. For example, to perform the training for machine learning model 304a, patient data 364a of a first group of patients having data categories $S_0$, $S_1$, $S_2$, $S_3$ required by machine learning model 304a can be identified. Moreover, to perform the training for machine learning model 304b, patient data 364b of a second group of patients having data categories $S_2$, $S_4$, $S_5$ required by machine learning model 304b can be identified.

The group of patients identified for each training model, and their patient data, can then be divided into a first subset and a second subset. The first subset can be about 80% of the patient data (of the group of patients), whereas the second subset can be about 20%. The patient data of the first subset of the group of patients can be used to train the machine learning model, while the patient data of the second subset of the group of patients can be used to generate the performance metric (e.g., AUC of ROC) of the trained machine learning model. For example, as shown in FIG. 3A, patient data 366a, which is a first subset of patient data 364a, can be used to perform a training process 368 of machine learning model 304a. As explained above, in a case where the machine learning model classifies a patient into one of a group (e.g., a random forest decision tree), the training can be based on, for example, maximizing the similarity in the survival statistics of the patients within a group and maximizing the difference in the survival statistics of the patients between different groups. In a case where the machine learning model comprises a regression model, the training can be based on fitting the parameters of the regression model to the survival statistics of the patients.

Moreover, patient data 366b, which is a second subset of patient data 364a, can be input to the trained machine learning model 304a in a validation process 370 to determine the performance metric (e.g., AUC), as described in FIG. 3C. Then, at process 372, the weight $M_A$ of machine learning model 304a (e.g., based on Equation 2 above) can be determined using the performance metric In addition, patient data 376a, which is a first subset of patient data 364b, can be used to performing a training process 378 of machine learning model 304b, whereas patient data 376b, which is a second subset of patient data 364b, can be input to the trained machine learning model 304b in a validation process 380 to determine the performance metric (e.g., AUC) of machine learning model 304b, followed by determining the weight $M_B$ of machine learning model 304b (e.g., based on Equation 2 above) in process 382. The model parameters (e.g., the thresholds x0, s1, s2, x5, etc. in FIG. 2C, the regression parameters b0, b1, bn, etc. in FIG. 2D) of the machine learning models generated in steps 368 and 378, as well as the weights associated with the machine learning models generated in steps 370 and 380, can then be stored in machine learning model database 302 of FIG. 3A, and can be retrieved to construct a meta-model as described above.

In some examples, the training and the cross-validation of a machine learning model can be repeated in a number of iterations. For each iteration, different subsets of the patient data (e.g., different 80% and 20% portions of the patients) can be selected to perform the aforementioned training and validation operations, and the weight of the machine learning model can be determined by averaging the ROC areas from the multiple iterations. With more iterations of training and cross-validation, the confidence level of the machine learning models in generating the correct predictions can be improved.

V. Experimental Results

A. Overview of Experimental Method

The aforementioned meta-model techniques are tested using clinical patient data from the Flatiron Health clinical DataMarts for patients with three tumor types: metastatic colorectal cancer, metastatic breast cancer, and advanced lung cancer. A set of individual prediction models are developed, each performing a prediction of the survival rate of a patient based on a different set of data categories, for metastatic colorectal cancer, metastatic breast cancer and advanced lung cancer. In this experiment, eight individual prediction models are developed for metastatic colorectal cancer, seven individual prediction models are developed for metastatic breast cancer, while five individual prediction models are developed for advanced lung cancer. Each individual model is trained and tested using clinical patient data of patients that have all the requisite data categories for that model. The individual prediction models for each tumor type are then combined and retrained into a meta-model for each tumor type. The meta-model for each tumor type, and its constituent individual prediction models, are evaluated based on the performance metric AUC.

B. Patient Cohorts and Data Categories

Three patient cohorts, one for each of metastatic colorectal cancer, metastatic breast cancer, and advanced lung cancer, are defined from three Flatiron DataMarts: Metastatic CRC (colorectal cancer); ii) Advanced NSSLC (non-small cell lung cancer) iii) Metastatic Breast Cancer. For each patient in a patient cohort, the patient's outcome data of survival are extracted. The patient's outcome data of survival can be either the time between death and the date of advanced diagnosis, or between the date of the last recorded visit and the date of advanced diagnosis if no listed date of death.

In addition, various data categories of each patient that can be potential predictors for the survival rate of another patient having the same data categories are extracted. FIG. 4A illustrates the data categories input selected and input to each individual prediction model for each tumor type. The data categories can include laboratory test results, biographical data, medical history data, biomarkers, etc., as discussed in FIG. 2A.

For laboratory test results (labelled as "lab" in FIG. 4A), available results for selected quantitative laboratory tests were extracted for each patient in each cohort for specimens collected around the time (within +/−90 days) of the advanced diagnosis. Minimum and maximum test results for the patient are extracted and transformed into absolute median deviations (the absolute value of the result minus the population median) for use in the models. The use of absolute median deviation in the models can reflect the notion that for many tests, high or low values can be diagnostically informative. In addition, biography data such as age and gender, as well as medical history data, such as cancer stage, are also extracted.

Different biomarker data are also extracted for different cancer types. For example, for the CRC cohort, the KRAS and BRAF gene expression statuses of the patients in the cohort are extracted. For the breast cancer cohort, the patient's ER, PR and HER2 status are extracted. Further, for the lung cancer cohort, ALK and EGFR mutation status are extracted. For the molecular biomarkers (ER, PR, HER2, KRAS, BRAF, EGFR, ALK), we considered only the result for each marker on each patient nearest in time (e.g., based on specimen collect date) to the advanced diagnosis date. The molecular biomarker results are then classified as "positive", "negative" or "other," with "positive" indicating that the corresponding marker expression level being above a threshold, or a mutation was present. A "negative" classification indicated that the marker was absent or the mutation was not observed, and "other" indicated an equivocal result, a test that was not able to be performed or other non-definitive result.

C. Predictor Sets

Few if any patients had data for all of the potential predictors (lab tests, molecular biomarkers and clinical/ demographic variables) for survival rate prediction as shown in FIG. 4A. In this experiment, individual prediction models are developed for each tumor type, with each individual prediction model built and trained using a subset of the potential predictors. The individual prediction models are then combined into meta-models. As shown in FIG. 4A, seven individual prediction models are developed for metastatic colorectal cancer (labelled $CRC_A$-$CRC_G$ in FIG. 4A), five individual prediction models are developed for metastatic breast cancer (labelled $BC_A$-$BC_E$ in FIG. 4A), whereas eight individual prediction models are developed for advanced lung cancer (labelled $LC_A$-$LC_H$ in FIG. 4A). Each individual prediction model receives a set of predictors represented by a set of data categories as inputs to perform a prediction. For each prediction model, a data category labelled as "1" indicates that the data category is used to train the prediction model, whereas a data category labelled as "0" indicates that the data category is not used to train the prediction model. For example, the prediction model $LC_A$ for advanced lung cancer is trained based on gender and race data of patients and have the data categories for gender and race labelled as "1" in FIG. 4A. Moreover, the prediction model $LC_B$ for advanced lung cancer is trained based on age, histology, and smoking status, and have those data categories labelled as "1" in FIG. 4A.

Depending on the data categories (e.g., a number of the data categories, a distribution of the data categories are among the patient cohorts, etc.) represented by the predictor sets, each individual prediction model can be trained using clinical data of different proportions of the patient cohort of the corresponding tumor type that include the data categories. The different portions of the patient cohort can overlap, so that the same patient can be represented in multiple portions of the patient cohort, and the patient's clinical data are used to train multiple individual predictor models for the tumor type corresponding to the patient cohort.

FIG. 4B illustrates the portion of a patient cohort, for each tumor type, that has the requisite data categories for each individual prediction model. As shown in FIG. 4B, individual prediction model $CRC_A$ for metastatic CRC is trained based on the clinical data of 100% of the corresponding patient cohort. This can be due to, for example, only two data categories (gender and race) being provided as inputs the model, and the two data categories are common and present in the clinical data of all patients. In addition, individual prediction models $CRC_B$ and $CRC_C$ for metastatic $CR_C$, individual prediction models $BC_A$-$BC_D$, as well as individual prediction models $LC_A$-$LC_C$ for advanced lung cancer, are trained based on a relatively large portion (94%-100%) of the clinical data of the corresponding patient cohort for similar reasons.

In contrast, individual prediction model $CRC_G$ is trained based on the clinical data of only 15% of the corresponding patient cohort. This can be due to, for example, a large number of data categories being input to the model, and a few of them (e.g., biomarkers) are present only in the clinical data of a small portion of the patient cohort. In addition, individual prediction models $CRC_D$-$CRC_G$ for metastatic CRC, individual prediction model $BC_E$, as well as individual prediction models $LC_D$-$LC_H$ for advanced lung cancer, are trained based on a relatively small portion (2%-63%) of the clinical data of the corresponding patient cohort for similar reasons.

D. Individual Prediction Model and Meta-Data

The identified portions of clinical data having the requisite data categories for each individual prediction model, as shown in FIG. 4B, are then used to build and train the individual prediction models. In a first part of the experiment, each individual prediction model includes a random forest model as described in FIG. 2C. In a second part of the experiment, each individual model includes a mathematical model, as described in FIG. 2D. Each portion of the clinical data is split randomly in an approximately 75:25 ratio into a training and a test partition, respectively. The training partition was used for model development, whereas the test partition was held aside for testing the meta-model as to be described below.

The training partition is further split into a first subset of clinical data to perform training of the individual prediction model, and a second subset of clinical data to validate the performance of the trained model, as described in FIG. 3D. For example, 80% of the training partition can be used for training, whereas 20% of the training partition can be used for validation. Five different splits can be performed to create five different first and second subset of the clinical data. The validation partition is used to compute the AUC for the trained model for survival rate at 500, 1000, and 1500 days after diagnosis, in a cross-validation operation, as shown in FIG. 3C. The training and validation operations are performed five times with the different training and validation partitions to obtain five AUC values. The weight of each individual prediction model is then determined based on an average of the five AUC values obtained from the training and validation operations.

E. Experiment Results

A meta-model for each tumor type (metastatic colorectal cancer, metastatic breast cancer, and advanced lung cancer) is then tested using the test partition. Two sets of tests are performed. The first test includes performing patient-specific survival rate prediction using a meta-model for randomly selected patients, whereas the second test includes determining the AUCs of the meta-models.

In the first test, a random group of patients are selected from the test partition of each patient cohort. For each patient, the individual prediction models for which the patient has the requisite data categories are identified and combined using the weights associated with the individual prediction models, to form a meta-model, as described in FIG. 3A. The meta-model is then used to determine the survival rate at various time points from the time diagnosis, to generate a K-M plot for the patients.

Figure 4C:
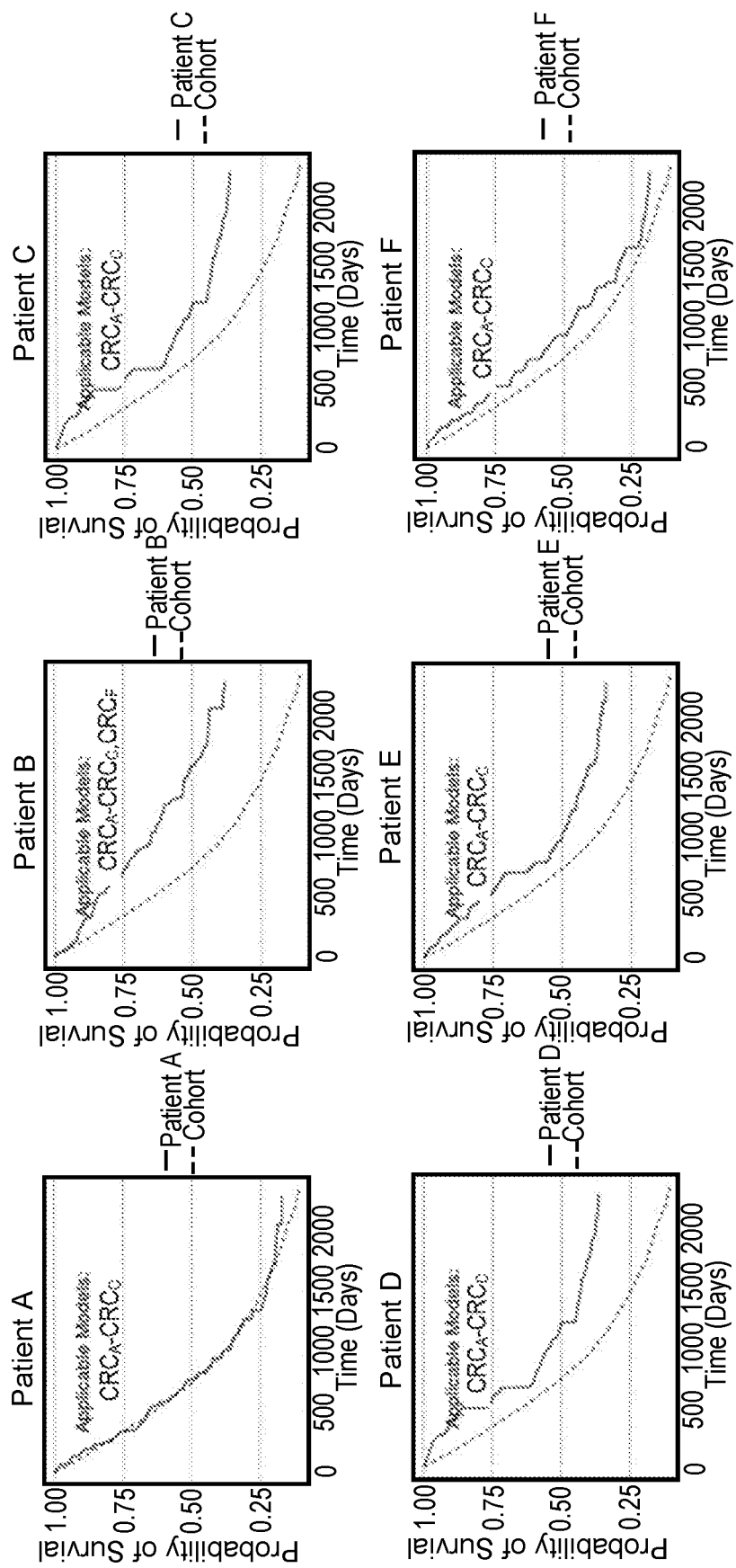

FIG. 4C illustrates the K-M plot of meta-models of 12 patients (patients A-L) from the patient cohort of the metastatic CRC (represented in solid lines), as wells as the K-M plot of the patients represented in the training partition of the patient cohort (represented in dotted lines). The K-M plots in FIG. 4C illustrates that the survival rates of a particular patient can be vastly different from the survival rates of a cohort. As shown in FIG. 4C, the patients can have different sets of applicable individual prediction models. For example, patient A has applicable prediction models $CRC_A$, $CRC_B$, and $CRC_C$ (represented as $CRC_A$-$CRC_C$ in FIG. 4C), whereas patient H has applicable prediction models $CRC_A$, $CRC_B$, $CRC_C$, $CRC_D$, $CRC_E$, $CRC_F$, and $CRC_G$ (represented as $CRC_A$-$CRC_G$ in FIG. 4C). In addition, besides patient A, the K-M plots of other patients do not conform with the K-M plot of the training partition of the patient cohort. This further highlights the need to provide patient-specific survival prediction rather than relying on population-based survival statistics.

In the second test, the AUCs of meta-models are determined and compared with the AUCs of the individual prediction models. Specifically, referring back to FIG. 3C, for each patient in the training partition, individual prediction models for which the patient has the requisite data categories are determined, and a meta-model is obtained by combining the identified individual prediction models. A survival rate or the patient is determined for the patient using the metal model and compared with a probability threshold to predict whether the patient survives at a particular time after diagnosis (e.g., 500 days, 1000 days, and 1500 days). The actual survival information of that patient is compared with the survival prediction to count the patient as a true positive or a false positive. The analysis is performed for all patients within the training partition and for different probability thresholds to generate an AUC for the meta-model approach.

Figure 4D:
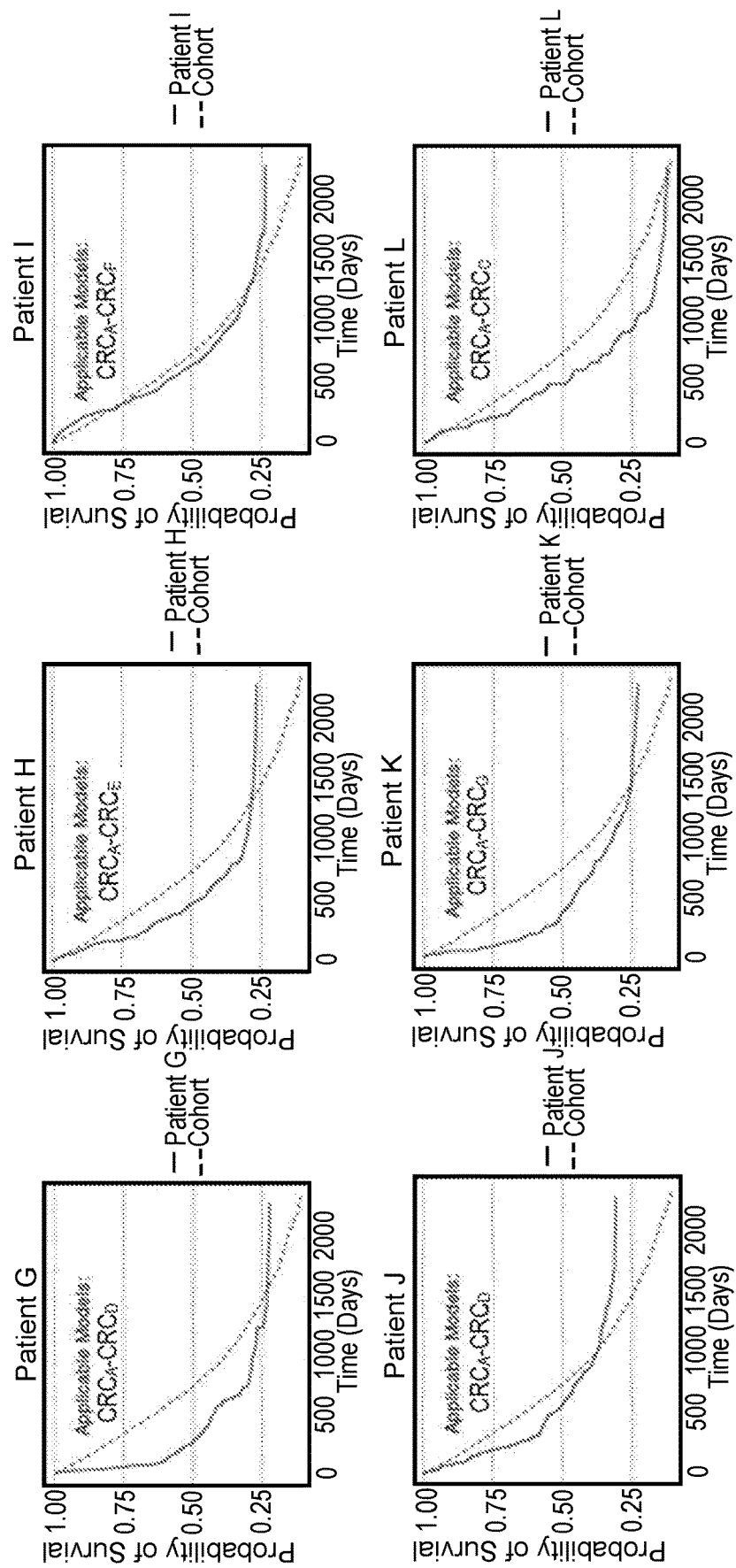
Figure 4E:
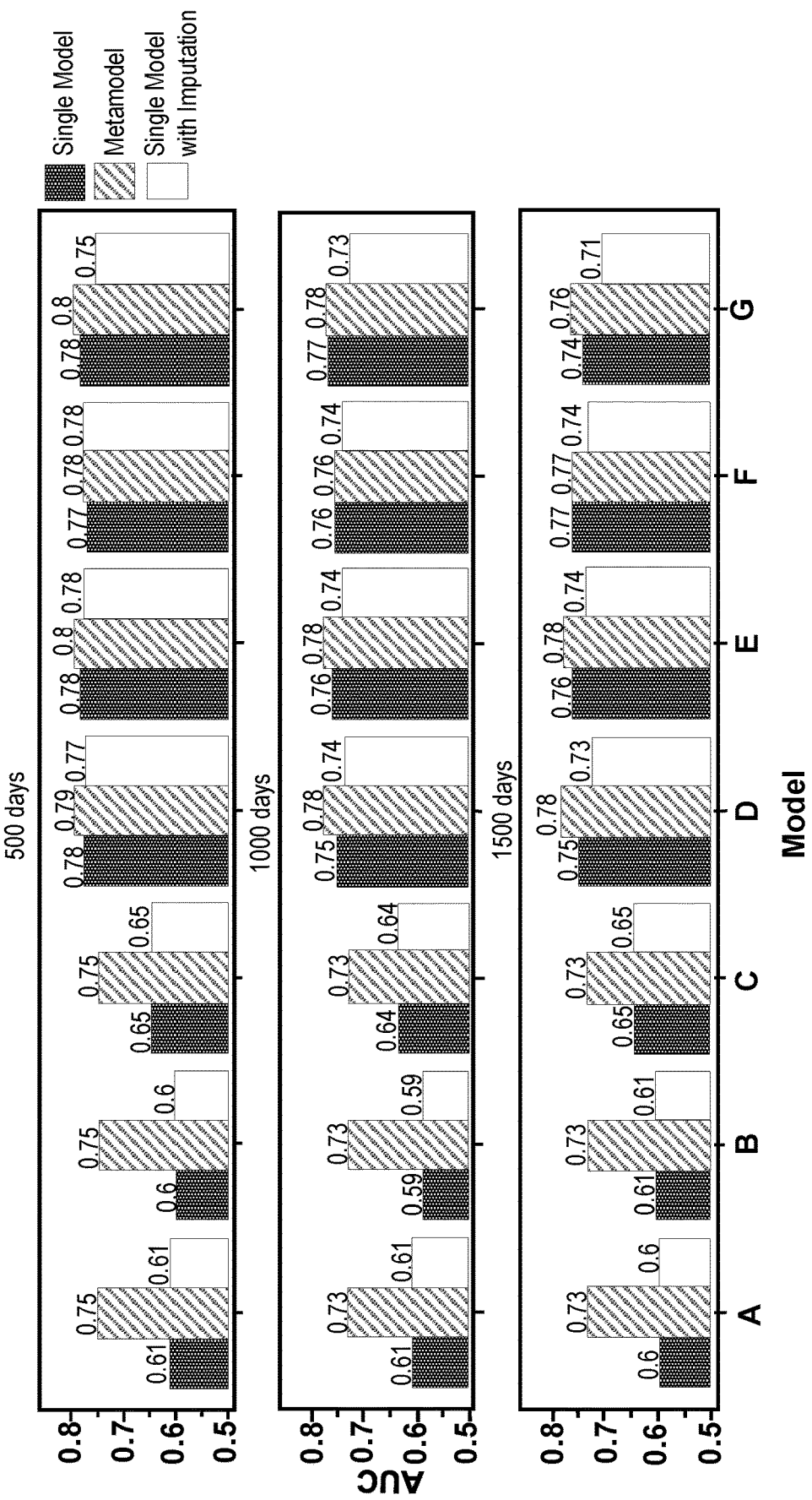

FIG. 4D illustrates the AUCs of each individual prediction model, and meta-model for the metastatic CRC patient cohort in the second test. The meta-models represented in the AUC plot can include different sets of prediction models based on the data categories present in the patients data used to evaluate each prediction model. In FIG. 4D, the AUCs are computed as follows: a) a prediction model using only a subset of the patients data having the requisite data categories; b) a metal-model comprising all the prediction models for which the subset of the patients data have the requisite data categories; and c) the prediction model using all the patients data, and for those who do not have the requisite data categories, imputed data are used for the missing data categories.

As shown in FIG. 4D, the meta-model approach provide improved AUCs compared with each individual prediction model. Substantial improvement in the AUC can be observed in a case where the individual prediction model only receives a small set of data categories as inputs (e.g., prediction model $CRC_A$ which only uses gender and race). For example, for survival rate prediction at 500 days and 1000 days, the AUC is improved from 0.61 using only prediction model $CRC_A$ to 0.74 using the meta-model approach. Moreover, for survival rate prediction at 1500 days, the AUC is improved from 0.57 using only prediction model $CRC_A$ to 0.74 using the meta-model approach.

Even for prediction models that receive a large number of data categories as inputs (e.g., prediction model $CRC_G$), there is improvement in the AUC. For example, for survival rate prediction at 500 days, the AUC is improved from 0.81 using only prediction model $CRC_G$ to 0.84 using the meta-model approach. Moreover, for survival rate prediction at 1000 days, the AUC is improved from 0.78 using only prediction model $CRC_G$ to 0.79 using the meta-model approach. Further, for survival rate prediction at 1500 days, the AUC is improved from 0.73 using only prediction model $CRC_G$ to 0.75 using the meta-model approach.

In addition, the AUC of a meta-model is also higher than the AUC of a single model using imputed data for all prediction models. This can be due to the imputed data being generated based on the "missing at random" assumption, but this is not a valid assumption in the clinical data, as explained above.

VI. Method

Figure 5:
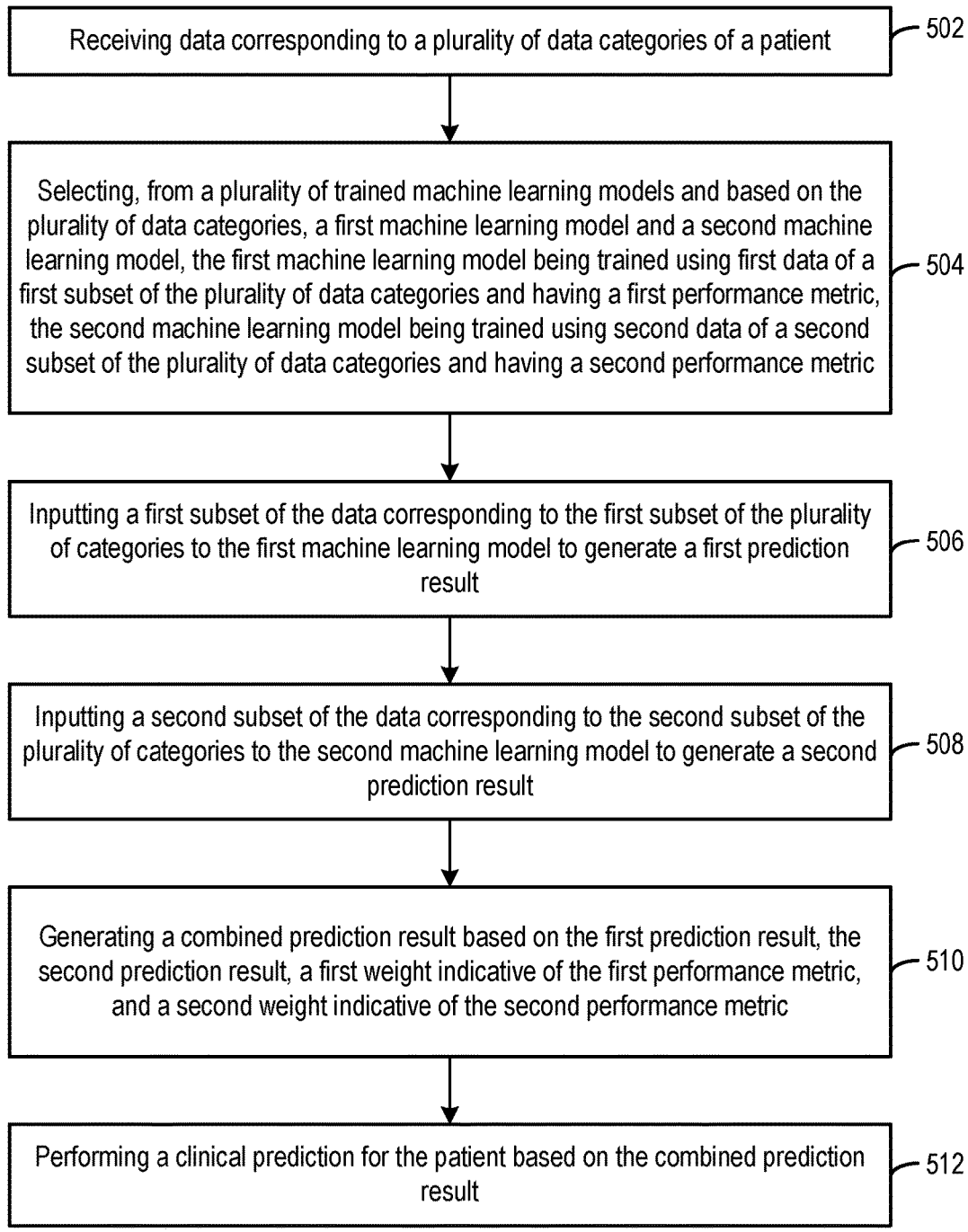
FIG. 5 illustrates a method of preforming a clinical prediction, according to certain aspects of this disclosure.

FIG. 5 illustrates a method 500 of preforming a clinical prediction for a patient. The clinical prediction can include, for example, a survival rate of the patient at a particular time after a disease diagnosis (e.g., a particular type of cancer). Method 500 can be performed by various components of clinical prediction system 300.

In step 502, clinical prediction system 300 (e.g., select module 304) receives data 308 corresponding to a plurality of data categories of a patient. The plurality of data categories can include, for example, biographical data, medical history data, laboratory test results, biomarkers, etc., as shown in FIG. 4A.

In step 504, clinical prediction system (e.g., select module 304) selects, from a plurality of trained machine learning models and based on the plurality of data categories, a first machine learning model and a second machine learning model, the first machine learning model being trained using first data of a first subset of the plurality of data categories and having a first performance metric, the second machine learning model being trained using second data of a second subset of the plurality of data categories and having a second performance metric. The machine learning models can be selected from machine learning models database 302 of clinical prediction system 300.

Specifically, machine learning models database 302 of clinical prediction system 300 may store a plurality of machine learning models including model 304a, 304b, 304c, etc. Each machine learning model can include, for example, a random forest model (e.g., random forest model 230 of FIG. 2C), a regression model (e.g., regression model 250 of FIG. 2D), or other types of machine learning models, to perform a prediction (e.g., survival rate). Each machine learning model in machine learning model database 302 is separately trained using data of a set of data categories to perform the prediction, and different machine learning models are trained using data of different sets of data categories, although there can be overlapping data categories among the different sets. For example, referring to FIG. 3A, in a case where data 308 includes data categories $S_0$, $S_1$, $S_2$, $S_3$, $S_4$, and $S_5$, select module 304 can identify first machine learning model 304a trained with data categories $S_0$, $S_1$, $S_2$, and $S_3$, as well as second machine learning model 304b trained with data categories $S_0$, $S_4$, $S_5$.

In addition, each of the plurality of machine learning models can be associated with a performance metric, such as AUC, which can be represented in the form of a weight. Select module 304 can perform a search of the machine learning models in machine learning models database 302 and identify the machine learning models for which the data, received in step 502, include the requisite data categories, and provide the identified machine learning models and their associated performance metrics (e.g., weights) to prediction module 306.

Referring back to FIG. 3A, select module 308 can perform, in machine learning models database 302, a search of machine learning models that accept a subset (or the entirety) of data categories present in data 308. In one example, select module 308 can obtain the requisite data categories of each and every machine learning model in the database (e.g., data categories $S_0$, $S_1$, $S_2$, and $S_3$ for machine learning model 304a, data categories $S_2$, $S_4$, and $S_5$ for machine learning model 304b, etc.), compare the data categories with those of data 308, and determine whether the requisite data categories of a machine learning model represent a subset (or the entirety) of the data categories in data 308. If they are, select module 308 can select the machine learning model to form the meta-model. Select module 308 can then provide the selected machine learning models to predictor module 306.

In step 506, a first subset of the data corresponding to the first subset of the plurality of the plurality of categories is input to the first machine learning model to generate a first prediction result. Referring to FIG. 3A, prediction module 306 can input a first subset of data 308 including data categories $S_0$, $S_1$, $S_2$, and $S_3$ to first machine learning model 304a. The first prediction result can include, for example, a first survival rate predicted for the patient by first machine learning module 304a.

In step 508, a second subset of the data corresponding to the second subset of the plurality of the plurality of categories is input to the second machine learning model to generate a second prediction result. Referring to FIG. 3A, prediction module 306 can input a second subset of data 308 including data categories $S_0$, $S_4$, $S_5$ to second machine learning model 304b. The second prediction result can include, for example, a second survival rate predicted for the patient by second machine learning module 304b.

In step 510, prediction module 306 generates a combined prediction result based on the first prediction result, the second prediction result, a first weight indicative of the first performance metric, and a second weight indicative of the second performance metric. For example, prediction module 306 can generate a combined survival rate for the patient based on a weighted average of the first survival rate and the second survival rate based on the first weight and the second weight. The first weight can reflect a first AUC of first machine learning model 304a, whereas the second weight can reflect a second AUC of second machine learning model 304b.

In step 512, a clinical prediction of the patient can be performed based on the combined prediction result. For example, the combined survival rate can then be provided to a clinical decision support tool, such as clinical decision support tool 104, to generate various information to support a clinical decision, as described above in FIG. 1B. For example, to facilitate care to the patient, clinical decision support tool 104 can generate information to allow the clinician to better assess the patient's prognosis, such as comparison between the patient's predicted survival rates with other patients, the patient's life expectancy, etc. The information can facilitate discussions between the clinician and the patient regarding the patient's prognosis as well as assessment of treatment options and the patient's planning of life events. As an illustrative example, if clinical decision support tool 104 predicts that the patient has a relatively long remaining life (e.g., 5 years), the patient may decide to undergo an aggressive treatment that is more physically demanding and has more serious side effects. But if clinical decision support tool 104 indicates that the patient has a relatively short remaining life (e.g., less than a year), the patient may decide to forgo the treatment or to undergo an alternative treatment, and plan for care and life events in the remainder of the patient's life.

In addition, clinical decision support tool 104 can also output information to facilitate a selection of optimal treatment for the patient. For example, clinical decision support tool 104 can display different K-M plots of the patient for different treatments based on the patient's data. The clinician can then select a treatment to, for example, maximize the survival rate of the patient at a given time, to maximize the expected remaining life of the patient, etc.

In all these examples, the clinical prediction made for the patient is more likely to be accurate, or at least more pertaining to that patient, as clinical prediction is made based on a survival rate predicted for a patient rather than a cohort of patients. As show in FIG. 4D, a patient-specific prediction of survival rate can be very different from the survival rate of a cohort of patients. The disclosed techniques can improve the accuracy and relevance of the clinical prediction, while avoiding the issues of missing data categories in a case where a machine learning model requires many data categories which a patient do not have.

VII. Computer System

Any of the computer systems mentioned herein may utilize any suitable number of subsystems. Examples of such subsystems are shown in FIG. 6 in computer system 10. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices. In some embodiments, a cloud infrastructure (e.g., Amazon Web Services), a graphical processing unit (GPU), etc., can be used to implement the disclosed techniques.

The subsystems shown in FIG. 6 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of means known in the art such as input/output (I/O) port 77 (e.g., USB, FireWire). For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of a plurality of instructions from system memory 72 or the storage device(s) 79 (e.g., a fixed disk, such as a hard drive, or optical disk), as well as the exchange of information between subsystems. The system memory 72 and/or the storage device(s) 79 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

Aspects of embodiments can be implemented in the form of control logic using hardware (e.g. an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, units, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the invention has been presented for the purposes of illustration and description. It is not intended to be exhaustive or to limit the invention to the precise form described, and many modifications and variations are possible in light of the teaching above.

A recitation of "a", "an" or "the" is intended to mean "one or more" unless specifically indicated to the contrary. The use of "or" is intended to mean an "inclusive or," and not an "exclusive or" unless specifically indicated to the contrary. Reference to a "first" component does not necessarily require that a second component be provided. Moreover reference to a "first" or a "second" component does not limit the referenced component to a particular location unless expressly stated.

All patents, patent applications, publications, and descriptions mentioned herein are incorporated by reference in their entirety for all purposes. None is admitted to be prior art.

What is claimed is:

1. A computer-implemented method of performing a clinical prediction, comprising:
   receiving patient medical data corresponding to a plurality of data categories of biological or behavioral characteristics or treatment history of a particular patient;
   selecting, from a plurality of trained machine learning models and based on the plurality of data categories of biological or behavioral characteristics or treatment history of the particular patient, a first machine learning model and a second machine learning model, the first machine learning model being trained using first clinical data of a first subset of the plurality of data categories and having a first clinical performance metric value, the second machine learning model being trained using second clinical data of a second subset of the plurality of data categories and having a second clinical performance metric value, the second subset of the plurality of data categories being different from the first subset of the plurality of data categories of biological or behavioral characteristics or treatment history, the training comprising:
      based on inputting the first clinical data to the first machine learning model, setting parameters of the first machine learning model; and
      based on inputting the second clinical data to the second machine learning model, setting parameters of the second machine learning model;
   inputting a first subset of the patient medical data corresponding to the first subset of the plurality of data categories of biological or behavioral characteristics or treatment history to the first machine learning model to generate a first clinical prediction result;
   inputting a second subset of the patient medical data corresponding to the second subset of the plurality of data categories of biological or behavioral characteristics or treatment history to the second machine learning model to generate a second clinical prediction result;
   generating a combined clinical prediction result based on the first clinical prediction result, the second clinical prediction result, a first weight indicative of the first clinical performance metric value, and a second weight indicative of the second clinical performance metric value, the second clinical performance metric value being different from the first clinical performance metric value;
   performing a clinical prediction for the particular patient based on the combined clinical prediction result; and
   outputting the clinical prediction that identifies a diagnosis or prognosis of a medical condition of the particular patient or a treatment to administer to the particular patient.

2. The method of claim 1, wherein the first subset of the plurality of data categories and the second subset of the plurality of data categories include at least one common data category.

3. The method of claim 1, wherein the data categories comprise at least one of: biography data of the particular patient, results of one or more chemical tests of the particular patient, biopsy image data of the particular patient, molecular biomarkers of the particular patient, a tumor site of the particular patient, or a tumor stage of the particular patient.

4. The method of claim 1, wherein the plurality of trained machine learning models comprises a third machine learning model trained using third data of a third data category, the third data category not being part of the plurality of data categories; and wherein the third machine learning model is not selected for the particular patient based on the third data category not present in the plurality of data categories of the particular patient.

5. The method of claim 1, wherein the clinical prediction comprises predicting a survival rate of the particular patient at a pre-determined time from when the particular patient is diagnosed of having a tumor at an advanced stage.

6. The method of claim 5, further comprising determining a treatment for the particular patient based on at least the predicted survival rate.

7. The method of claim 5, wherein the plurality of data categories comprises a category related to a treatment received by the particular patient; and wherein the clinical prediction comprises predicting a survival rate of the particular patient at the pre-determined time in response to the treatment.

8. The method of claim 5, wherein the first machine learning model and the second machine learning model comprise at least one of: a random forest model, or a hazard function.

9. The method of claim 8, wherein the first machine learning model and the second machine learning model comprises a random forest model, the random forest model comprising a plurality of decision trees each configured to process a subset of the first subset of the patient medical data to generate a cumulative hazard function (CHF) value; and wherein the survival rate of the particular patient at the pre-determined time is determined based on an average of the CHF values output by the plurality of decision trees.

10. The method of claim 8, wherein the first machine learning model comprises a hazard function which outputs a probability of non-survival of the particular patient at the pre-determined time, the hazard function being a function of values of the first subset of the plurality of data categories of biological or behavioral characteristics or treatment history.

11. The method of claim 10, wherein the first clinical performance metric value and the second clinical performance metric value refer to rates of correct prediction of survival and rates of false prediction of survival by the first machine learning model and the second machine learning model for a group of patients at the pre-determined time.

12. The method of claim 10, wherein the first clinical performance metric value and the second clinical performance metric value are based on an area under curve (AUC) of a receiver operating characteristic (ROC) curve of, respectively, the first machine learning model and the second machine learning model;

wherein the first weight is based on an area measurement of a first AUC of a first ROC curve of the first machine learning model; and wherein the second weight is based on an area measurement of a second AUC of a second ROC curve of the first machine learning model.

13. The method of claim 12, wherein the combined clinical prediction result represents a linear combination of the first clinical prediction result scaled by the first weight and the second clinical prediction result scaled by the second weight.

14. The method of claim 1, wherein the first clinical performance metric is determined based on the first clinical data; and wherein the second clinical performance metric value is determined based on the second clinical data.

15. The method of claim 14, wherein:
the first machine learning model is trained using a first subset of the first clinical data;
the first clinical performance metric value is determined based on outputs of the trained first machine learning model in processing a second subset of the first clinical data;
the second machine learning model is trained using a third subset of the second clinical data; and
the second clinical performance metric value is determined based on outputs of the trained second machine learning model in processing a fourth subset of the second clinical data.

16. The method of claim 15, wherein:
the first machine learning model is trained using different first subsets of the first clinical data;
the first clinical performance metric value is determined based on outputs of the trained first machine learning model in processing different second subsets of the first clinical data;
the second machine learning model is trained using different third subsets of the second clinical data; and
the second clinical performance metric value is determined based on outputs of the trained second machine learning model in processing different fourth subsets of the second clinical data.

17. A non-transitory computer readable medium storing instructions that, when executed by a hardware processor, causes the hardware processor to:
receive patient medical data corresponding to a plurality of data categories of biological or behavioral characteristics or treatment history of a particular patient;
select, from a plurality of trained machine learning models and based on the plurality of data categories of biological or behavioral characteristics or treatment history of the particular patient, a first machine learning model and a second machine learning model, the first machine learning model being trained using first clinical data of a first subset of the plurality of data categories and having a first clinical performance metric value, the second machine learning model being trained using second clinical data of a second subset of the plurality of data categories of biological or behavioral characteristics or treatment history and having a second clinical performance metric value, the training comprising:
based on inputting the first clinical data to the first machine learning model, setting parameters of the first machine learning model; and
based on inputting the second clinical data to the second machine learning model, setting parameters of the second machine learning model;
input a first subset of the patient medical data corresponding to the first subset of the plurality of data categories of biological or behavioral characteristics or treatment history to the first machine learning model to generate a first clinical prediction result;
input a second subset of the patient medical data corresponding to the second subset of the plurality of data categories of biological or behavioral characteristics or treatment history to the second machine learning model to generate a second clinical prediction result;

generate a combined clinical prediction result based on the first clinical prediction result, the second clinical prediction result, a first weight indicative of the first clinical performance metric value, and a second weight indicative of the second clinical performance metric value;

perform a clinical prediction for the particular patient based on the combined clinical prediction result; and outputting the clinical prediction that identifies a diagnosis or prognosis of a medical condition of the particular patient or a treatment to administer to the particular patient.

18. The non-transitory computer readable medium of claim 17, wherein the categories of biological or behavioral characteristics or treatment history comprise at least one of: biography data of the particular patient, results of one or more chemical tests of the particular patient, biopsy image data of the particular patient, molecular biomarkers of the particular patient, a tumor site of the particular patient, or a tumor stage of the particular patient;

wherein the clinical prediction comprises predicting a survival rate of the particular patient at a pre-determined time from when the particular patient is diagnosed of having a tumor at an advanced stage; and wherein the first machine learning model and the second machine learning model comprise at least one of: a random forest model, or a hazard function.

19. A system comprising:

a memory that stores a set of instructions; and a hardware processor configured to execute the set of instructions to:

receive patient medical data corresponding to a plurality of data categories of biological or behavioral characteristics or treatment history of a particular patient;

select, from a plurality of trained machine learning models and based on the plurality of data categories of biological or behavioral characteristics or treatment history of the particular patient, a first machine learning model and a second machine learning model, the first machine learning model being trained using first clinical data of a first subset of the plurality of data categories and having a first clinical performance metric value, the second machine learning model being trained using second clinical data of a second subset of the plurality of data categories and having a second clinical performance metric value, the training comprising:

based on inputting the first clinical data to the first machine learning model, setting parameters of the first machine learning model; and based on inputting the second clinical data to the second machine learning model, setting parameters of the second machine learning model;

input a first subset of the patient medical data corresponding to the first subset of the plurality of data categories of biological or behavioral characteristics or treatment history to the first machine learning model to generate a first clinical prediction result;

input a second subset of the patient medical data corresponding to the second subset of the plurality of data categories of biological or behavioral characteristics or treatment history to the second machine learning model to generate a second clinical prediction result;

generate a combined clinical prediction result based on the first clinical prediction result, the second clinical prediction result, a first weight indicative of the first clinical performance metric value, and a second weight indicative of the second clinical performance metric value;

perform a clinical prediction for the particular patient based on the combined clinical prediction result; and outputting the clinical prediction that identifies a diagnosis or prognosis of a medical condition of the particular patient or a treatment to administer to the particular patient.

20. The system of claim 19, wherein the data categories of biological or behavioral characteristics or treatment history comprise at least one of: biography data of the particular patient, results of one or more chemical tests of the particular patient, biopsy image data of the particular patient, molecular biomarkers of the particular patient, a tumor site of the particular patient, or a tumor stage of the particular patient;

wherein the clinical prediction comprises predicting a survival rate of the particular patient at a pre-determined time from when the particular patient is diagnosed of having a tumor at an advanced stage; and wherein the first machine learning model and the second machine learning model comprise at least one of: a random forest model, or a hazard function.

* * * * *